United States Patent
Baker et al.

(10) Patent No.: US 9,664,680 B2
(45) Date of Patent: May 30, 2017

(54) METHODS OF DIAGNOSING PROLIFERATIVE DISORDERS

(71) Applicant: UNIVERSITY OF CENTRAL LANCASHIRE, Lancashire (GB)

(72) Inventors: Matthew James Baker, Lytham St Annes (GB); Peter Abel, Southport (GB); Robert William Lea, Preston (GB)

(*) Notice: Subject to any disclaimer, the term of this patent is extended or adjusted under 35 U.S.C. 154(b) by 0 days.

(21) Appl. No.: 15/059,797

(22) Filed: Mar. 3, 2016

(65) Prior Publication Data

US 2016/0252510 A1    Sep. 1, 2016

Related U.S. Application Data

(63) Continuation of application No. 14/443,134, filed as application No. PCT/GB2013/053005 on Nov. 14, 2013, now abandoned.

(30) Foreign Application Priority Data

Nov. 15, 2012   (GB) .................................. 1220573.8

(51) Int. Cl.

| | | |
|---|---|---|
| *G01N 33/49* | (2006.01) | |
| *G01N 33/574* | (2006.01) | |
| *G01N 21/552* | (2014.01) | |
| *G01N 33/00* | (2006.01) | |

(Continued)

(52) U.S. Cl.
CPC ..... *G01N 33/57407* (2013.01); *G01N 21/552* (2013.01); *G01N 33/49* (2013.01);
(Continued)

(58) Field of Classification Search
CPC .................. G01N 21/35; G01N 21/63; G01N 2021/3196; G01N 2021/3595;
(Continued)

(56) References Cited

U.S. PATENT DOCUMENTS

| | | | |
|---|---|---|---|
| 2004/0206905 A1 | 10/2004 | Chudner | |
| 2008/0254481 A1* | 10/2008 | Love | G01N 33/564 |
| | | | 435/7.1 |

(Continued)

FOREIGN PATENT DOCUMENTS

| | | |
|---|---|---|
| EP | 2 299 259 A1 | 3/2011 |
| WO | 97/14961 A1 | 4/1997 |

(Continued)

OTHER PUBLICATIONS

Khanmohammadi, M. et al, "Cancer diagnosis by discrimination between normal and malignant human blood samples using attenuate total reflectance-Fourier transform infrared spectroscopy," Cancer Invest., 2007, 25, 397-404.

(Continued)

*Primary Examiner* — Jennifer Wecker
(74) *Attorney, Agent, or Firm* — Barnes & Thornburg LLP

(57) ABSTRACT

The present invention relates to methods of diagnosing and/or prognosing proliferative disorders, especially brain cancers (e.g. gliomas). In particular, the present invention provides a means to conveniently detect malignant tumours merely by assaying or analysing blood (particularly blood serum). Cytokines and/or angiogenesis factors in blood serum have been found to be surprisingly powerful at indicating the presence of brain cancers in a subject. Moreover, spectroscopic analysis, especially ATR-FTIR analysis, of a blood sample has been demonstrated to be surprisingly effective at producing a signature that can be correlated with the presence, extent, severity, or aggressiveness of malignant tumours in a subject.

20 Claims, 18 Drawing Sheets

(51) Int. Cl.
| | |
|---|---|
| G01N 33/566 | (2006.01) |
| C40B 30/04 | (2006.01) |
| G01N 21/35 | (2014.01) |
| G01J 3/433 | (2006.01) |
| G01N 21/63 | (2006.01) |
| G01N 30/74 | (2006.01) |
| G01N 21/31 | (2006.01) |

(52) U.S. Cl.
CPC ............ *G01N 33/574* (2013.01); *G01J 3/433* (2013.01); *G01N 21/35* (2013.01); *G01N 21/63* (2013.01); *G01N 2021/3196* (2013.01); *G01N 2021/3595* (2013.01); *G01N 2030/743* (2013.01); *G01N 2201/129* (2013.01); *G01N 2800/52* (2013.01); *G01N 2800/7028* (2013.01)

(58) Field of Classification Search
CPC ........... G01N 2201/129; G01N 33/574; G01N 2800/7028; G01N 2030/743; G01N 21/552; G01J 3/433
See application file for complete search history.

(56) References Cited

U.S. PATENT DOCUMENTS

| | | | | |
|---|---|---|---|---|
| 2009/0042229 | A1* | 2/2009 | Folkman | G01N 33/57484 435/23 |
| 2010/0130868 | A1* | 5/2010 | Hargrove | A61B 5/0075 600/473 |
| 2011/0003707 | A1* | 1/2011 | Goix | G01N 33/6893 506/9 |
| 2012/0231963 | A1* | 9/2012 | Huang | G01N 33/57484 506/9 |

FOREIGN PATENT DOCUMENTS

| | | |
|---|---|---|
| WO | 2005/083440 A2 | 9/2005 |
| WO | 2010/129787 A2 | 11/2010 |
| WO | 2011/109810 A2 | 9/2011 |
| WO | 2011/151825 A2 | 12/2011 |
| WO | 2012/012693 A2 | 1/2012 |
| WO | 2013/072901 A | 5/2013 |

OTHER PUBLICATIONS

Hands, J. et al., "Investigating the rapid diagnosis of gliomas from serum samples using infrared spectroscopy and cytokine and angiogenesis factors," Analytical and Bioanalytical Chemistry, 2013, 405 7347-7355.

Peles, E et al., "Angiogenic factors in the cerebrospinal fluid of patients with astrocytic brain tumors," Neurosurg., 2004, 55, 562-568.

Sie, M. et al., "The Angiopoietin 1/Angiopoietin 2 Balance as a Prognostic Marker in Primary Glioblastoma Multiforme," J. Neurosurg., 110, 147-155.

Samaras, V. et al., "Analysis of interleukin (IL)-8 expression in human astrocytomas: Associations with IL-6, cyclooxygenase-2, vascular endothelial growth factor,and microvessel morphometry," Human Immunol., 2009, 70, 391-397.

Carlsson, A. et al., "Plasma proteome profiling reveals biomarker patterns associated with prognosis and therapy selection in glioblastoma multiforme patients," Proteomics Clin. Appl., 2010, 4, 591-602.

Tanase, C. et al., "Proteomic technologies in brain tumours early diagnosis," Eur. J. Cancer, 2010, Suppl. 8, Abs. 833.

Xu, B. J. et al., "Identification of blood protein biomarkers that aid in the clinical assessment of patients with malignant glioma," Int. J. Oncol., 2012, 40,1995-2003.

Ilhan-Mutlu, A., et al., "Exploratory investigation of eight circulating plasma markers in brain tumor patients," Neurosurg. Rev., 2013, 36, 45-56.

International (PCT) Search Report and Written Opinion prepared for PCT/GB2013/053005, mailed Feb. 5, 2014.

Guo, F. et al., "Tumor-derived hepatocyte growth factor is associated with poor prognosis of patients with glioma and Influences the chemosensitivity of glioma cell line to cisplatin in vitro," World Journal of Surgical Oncology, 2012, 10, 11 pages.

Riolfi, M. et al., "Leptin and Its Receptor are Overexpressed in Brain Tumors and Correlate with the Degree of Malignancy," Brain Pathology, 2010, 20, 481-489.

UK Search Report prepared for GB1220573.8, mailed Oct. 22, 2013.

UK Search Report prepared for GB1220573.8, mailed May 7, 2013.

Pan, Q. et al., "Investigation on Glioma Using FT-mid-IR Spectroscopy," Chemical Journal of Chinese Universities, 2012, 33, 1703-1707 (English abstract included).

Khanmohammadi, M. et al., "Application of Linear Discriminant Analysis and Attenuated Total Reflectance Fourier Transform Infrared Microspectroscopy for Diagnosis of Colon Cancer," Pathol. Oncol. Res., 2010, 17, 435-441.

* cited by examiner

Replacement Sheet 16 / 18

METHODS OF DIAGNOSING PROLIFERATIVE DISORDERS

CROSS-REFERENCE TO RELATED APPLICATIONS

This application is a Continuation of U.S. application Ser. No. 14/443,134, filed May 15, 2015, which is a national stage entry under 35 USC §371(b) of PCT International Application No. PCT/GB2013/053005, filed Nov. 14, 2013, and claims the benefit of United Kingdom Patent Application No. 1220573.8, filed on Nov. 15, 2012, the entire disclosures of which are expressly incorporated by reference herein.

FIELD OF THE INVENTION

The present invention relates to methods of diagnosing and/or prognosing proliferative disorders, especially brain cancers, such as gliomas. The invention also relates to the relevant diagnostic kits and associated analytical tools (e.g. databases, computer software, etc.).

BACKGROUND OF THE INVENTION

Proliferative disorders, such as cancer, are caused by uncontrolled and unregulated cellular proliferation. Such cellular proliferation can lead to the formation of tumours in the relevant subjects.

Typically tumours, such as brain tumours, are initially clinically identified within a subject by way of various well known pre-screening imaging techniques, such as computed tomography (CT), magnetic resonance imaging (MRI), X-Rays, and positron emission tomography (PET). Such imaging techniques are, however, expensive to deploy given the high cost of both the equipment itself and the human resources required to operate it. Some such imaging techniques require complex operation by highly qualified professionals, and some require time consuming analysis before conclusions can be drawn. Moreover, such techniques seldom, if ever, distinguish between benign and malignant tumours. As such, a final biopsy is always required to confirm the malignancy or benignity of a given tumour.

Biopsies require invasive surgery to extract a relevant tissue sample. In the case of brain tumours, biopsies generally require drilling into the subject's skull, which is a highly dangerous and skilled surgical operation. The subject having undergone such a biopsy is then typically hospitalised for two to three days, which presents an undesirable care burden. Once the biopsy has been successfully performed, it can take a significant period of time before the malignancy or benignity of the relevant tumour is actually determined.

It is therefore highly desirable to provide a pre-screening tool that is cost-effective, requires minimal human resource and skill to operate, and does not involve time consuming analysis. It is moreover desirable to provide a pre-screening technique that facilitates relatively fast determination of malignancy or benignity of tumours with a reasonably high degree of accuracy, and without the drawbacks inherent with biopsies.

In recent times, various biomarkers within the blood have been identified as useful indicators of particular diseases. For instance, cytokines, chemokines, and growth factors are cell signaling proteins that mediate a range of physiological responses, and are associated with various diseases. Such molecules are generally detected by either bioassay or immunoassay, both of which can be time consuming given that often only one analyte may be analysed at a time. However, in more recent times, magnetic bead-based multiplex assays designed to measure multiple cytokines, chemokines, and growth factors in diverse matrices like serum, plasma, and tissue culture supernatants, have become more readily available with kits such as Bio-Plex Pro™ (see Bio-Plex Pro™ Assay Handbook—http://www.bio-rad.com/webroot/web/pdf/lsr/literature/10014905.pdf). However, the complexities associated with the correlation of particular biomarkers with particular diseases has retarded developments in the medical diagnostics field, and such correlations are inherently unpredictable at present. Moreover, such assaying still requires a reasonable level of skill, and such assays also destroy the sample in question such that repeat assays on the same sample are not possible. Validation of results is thus more difficult.

In other developments in the field of medical diagnostics, a recent study has shown the potential of infra-red (IR) spectroscopy in the analysis of serum to discriminate myocardial infarction from other chest pain [Petrich W, Lewandrowski K B, Muhlestein J B, Hammond M E D, Januzzi J L, Lewandrowski E L, Pearson R R, Olenko B, Fruh J, Haass M, Hirschi M M, Kohler W, Mischler R, Mocks J, Ordonez-Llanos J, Quarder O, Somorjai R, Staib A, Sylven C, Werner G, Zerback R Analyst, 134(6), 2009; 1092-1098]. Spectroscopic diagnostic methods such as this could be highly desirable for both clinicians and patients if they could be made clinically viable, since they potentially offer a non-destructive, rapid, cost-effective, simple to operate point-of-care diagnosis of a condition. However, at present, it would appear that the applicability of such spectroscopic diagnostic techniques is somewhat limited in scope, given their questionable reliability in the face of sample variance.

It is therefore an object of the present invention to solve at least one of the problems inherent with the prior art. Another object is to provide a simple, reliable, and cost-effective point-of-care diagnostic method that requires minimal human resource and skill to operate, is non-time consuming, and which facilitates rapid determination of malignancy/benignity of tumours with a reasonably high degree of accuracy.

SUMMARY OF THE INVENTION

According to a first aspect of the present invention, there is provided a method of diagnosing and/or prognosing a brain cancer in a subject, the method comprising assaying a blood sample (or a component thereof) of the subject in respect of one or more (suitably predesignated) cytokines and/or angiogenesis factors.

According to a second aspect of the present invention, there is provided a method of diagnosing and/or prognosing a proliferative disorder in a subject, the method comprising performing spectroscopic analysis upon a blood sample (or component thereof) of the subject to produce a spectroscopic signature characteristic of the blood sample (or component thereof).

According to a third aspect of the present invention there is provided a method of detecting cancerous cells in a subject, comprising the steps of the method of diagnosing and/or prognosing a brain cancer or proliferative disorder of either the first or second aspect.

According to a fourth aspect of the present invention there is provided a method of diagnosing whether a tumour (suitably a brain tumour, e.g. a glioma) is malignant or benign, comprising the steps of the method of diagnosing and/or prognosing a brain cancer or proliferative disorder of either the first or second aspect.

According to a fifth aspect of the present invention, there is provided a method of monitoring a subject's responsiveness to surgical or therapeutic treatment of a proliferative disorder, comprising the steps of the method of diagnosing and/or prognosing a brain cancer or proliferative disorder of either the first or second aspect.

According to a sixth aspect of the present invention there is provided a diagnostic kit for diagnosing and/or prognosing a brain cancer in a subject, comprising a device configured to receive a blood sample (or component thereof) from the subject and assay the blood sample (or a component thereof) in respect of one or more (suitably predesignated) cytokines and/or angiogenesis factors; and a device (optionally the same as aforementioned) to correlate or facilitate correlation of the amounts of the one or more cytokines and/or angiogenesis factors within the blood sample (or component thereof) with a favourable or unfavourable diagnosis and/or prognosis.

According to a seventh aspect of the present invention there is provided a diagnostic kit for diagnosing and/or prognosing a proliferative disorder in a subject, comprising a device configured to receive a blood sample (or component thereof) from the subject and perform spectroscopic analysis upon the blood sample (or component thereof) of the subject to produce a spectroscopic signature characteristic of the blood sample (or component thereof); and a device (optionally the same as that aforementioned) to correlate or facilitate correlation of the spectroscopic signature of the blood sample (or component thereof) with a favourable or unfavourable diagnosis and/or prognosis.

According to a eighth aspect of the present invention there is provided a use of data from an assay of a blood sample (or a component thereof) of a subject in respect of one or more (suitably predesignated) cytokines and/or angiogenesis factors to determine a favourable or unfavourable diagnosis and/or prognosis of a brain cancer in the subject.

According to a ninth aspect of the present invention there is provided a use of a spectroscopic signature of a blood sample (or component thereof) of a subject to determine a favourable or unfavourable diagnosis and/or prognosis of a proliferative disorder in the subject.

According to a tenth aspect of the present invention, there is provided a database comprising a plurality of data sets, each set pertaining to the amounts of one or more cytokines and/or angiogenesis in a particular blood sample (or component thereof) of a particular subject, each set being correlated with a favourable or unfavourable diagnosis and/or prognosis in relation to a brain cancer in said particular subject.

According to an eleventh aspect of the present invention, there is provided a database comprising a plurality of spectroscopic signatures, each signature pertaining to a particular blood sample (or component thereof) of a particular subject, each signature being correlated with a favourable or unfavourable diagnosis and/or prognosis in relation to a proliferative disorder in said particular subject.

According to a twelfth aspect of the present invention, there is provided a computer-readable medium (e.g. a disc) comprising a database as defined herein.

According to a thirteenth aspect of the present invention, there is provided a computer installed with diagnostic computer software configured to operate the computer to perform a predictive diagnosis and/or prognosis in relation to a proliferative disorder based on a spectroscopic signature of a blood sample of a subject.

According to a fourteenth aspect of the present invention, there is provided a computer-readable medium containing diagnostic computer software as defined herein.

Suitably, the proliferative disorder is cancer, suitably a human cancer, suitably brain cancer (and/or associated tumours).

Features, including optional, suitable, and preferred features in relation to one aspect of the invention may also be features, including optional, suitable and preferred features in relation to any other aspect of the invention.

BRIEF DESCRIPTION OF THE DRAWINGS

Embodiments of the invention are further described hereinafter with reference to the accompanying drawings, in which.

DETAILED DESCRIPTION OF THE INVENTION

Definitions

Figure 1:
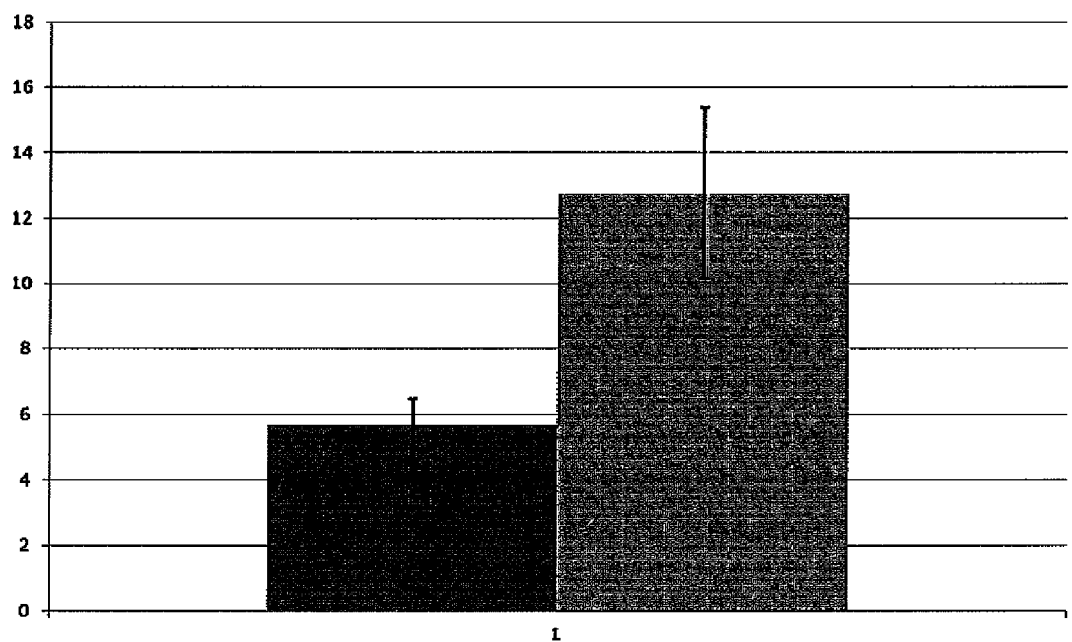
FIGS. 1 to 7 show graphical representations of the "control mean" (light grey) and "glioma mean" (dark grey), and also error bars, in relation to IL-8, Angiopoietin, Follistatin, HGF, Leptin, PDGF-BB, and PECAM-1 respectively.
Figure 2:
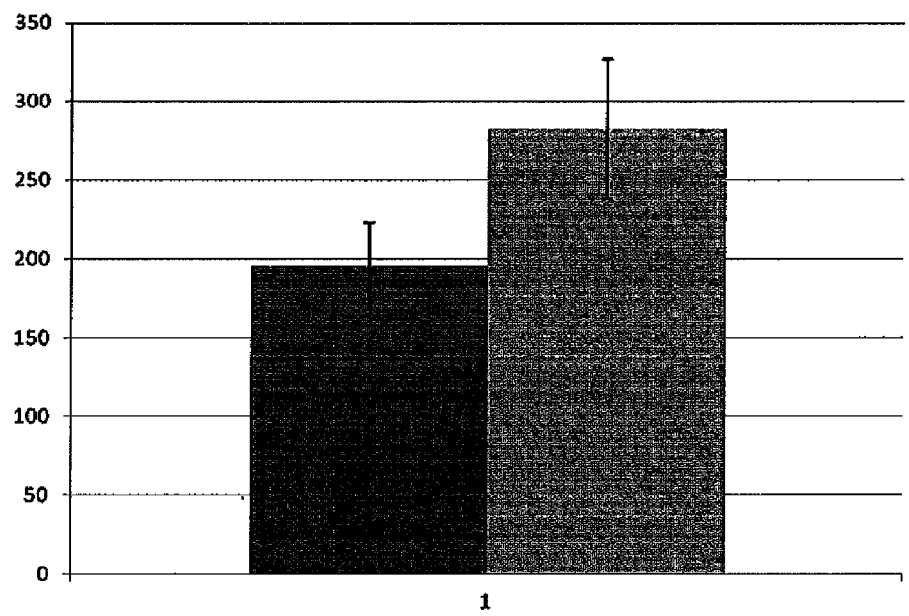
Figure 3:
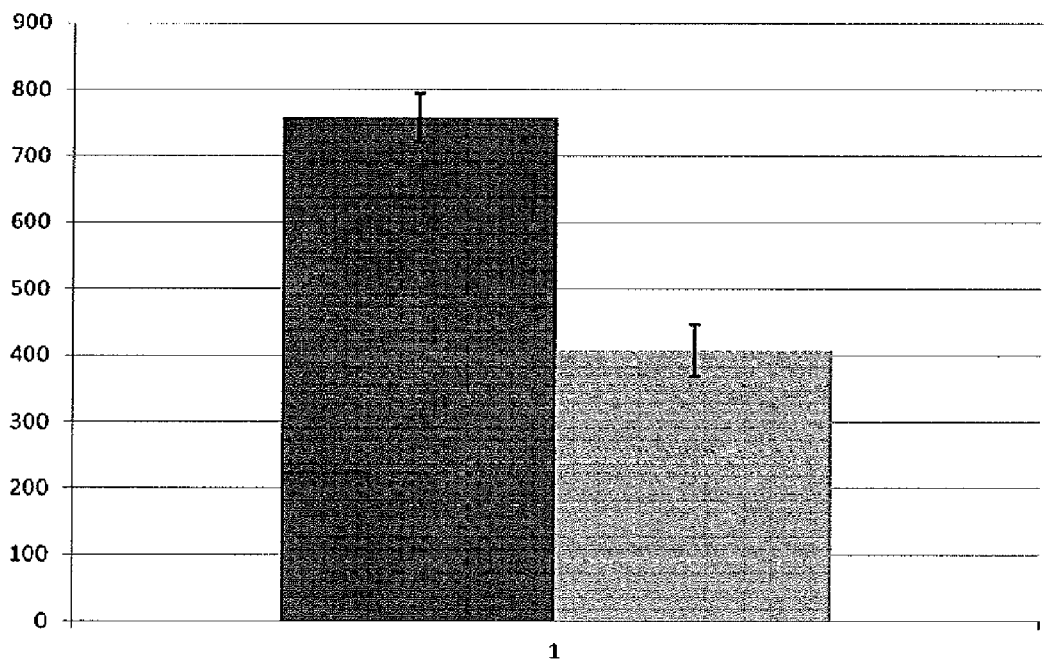
Figure 4:
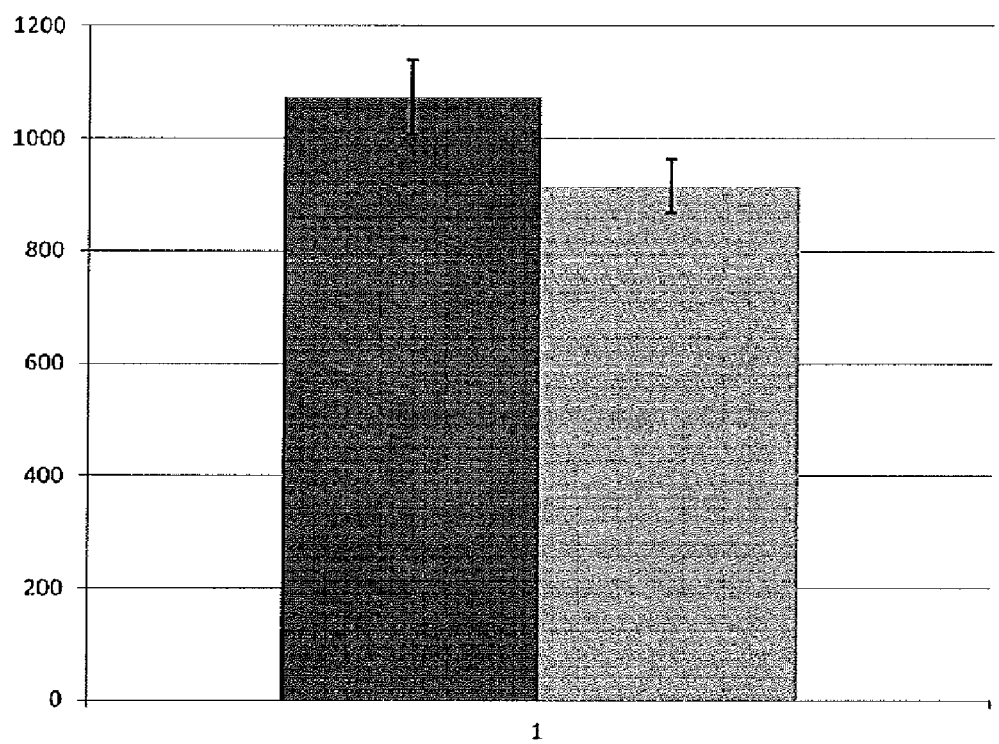
Figure 5:
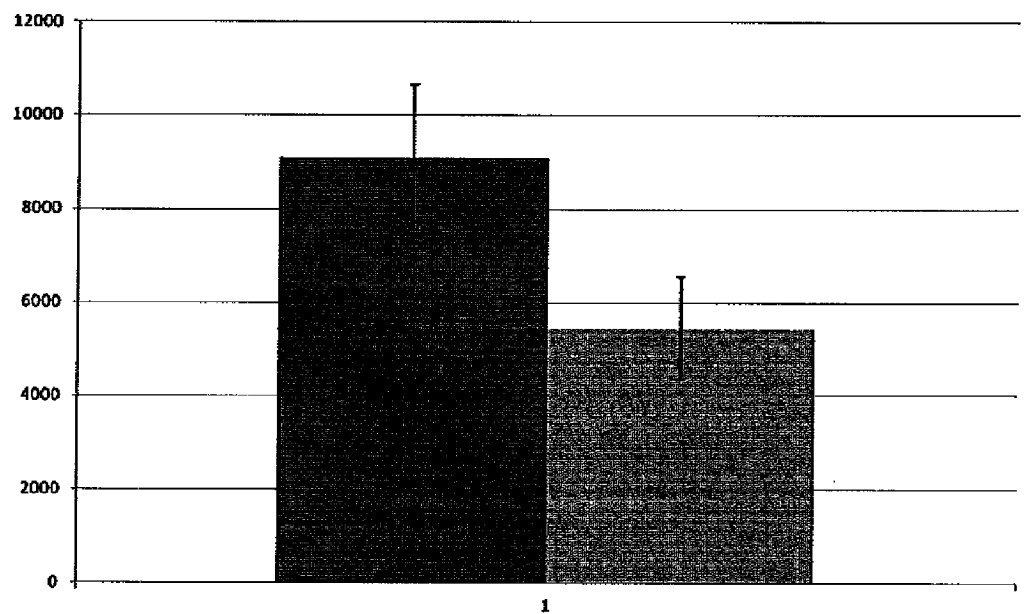
Figure 6:
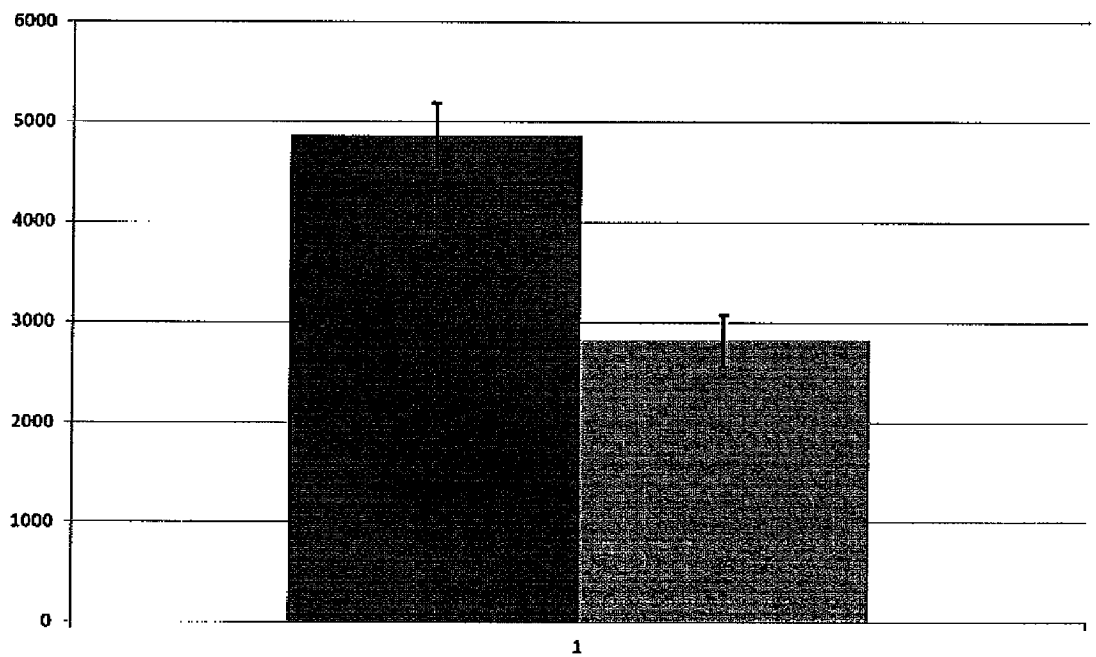
Figure 7:
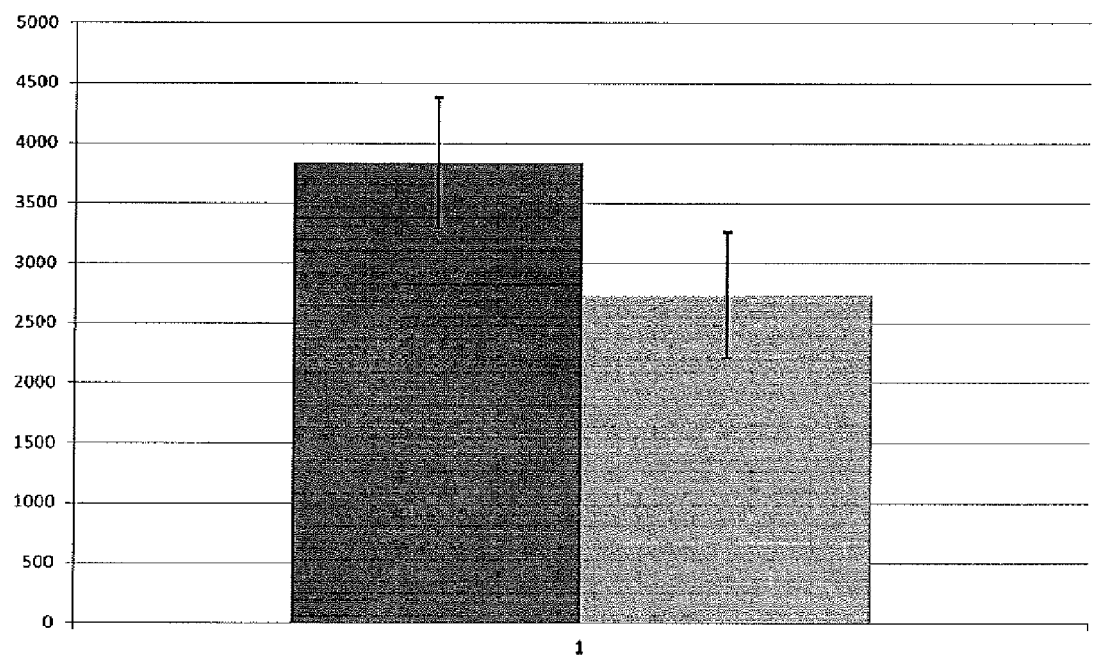
Figure 7A:
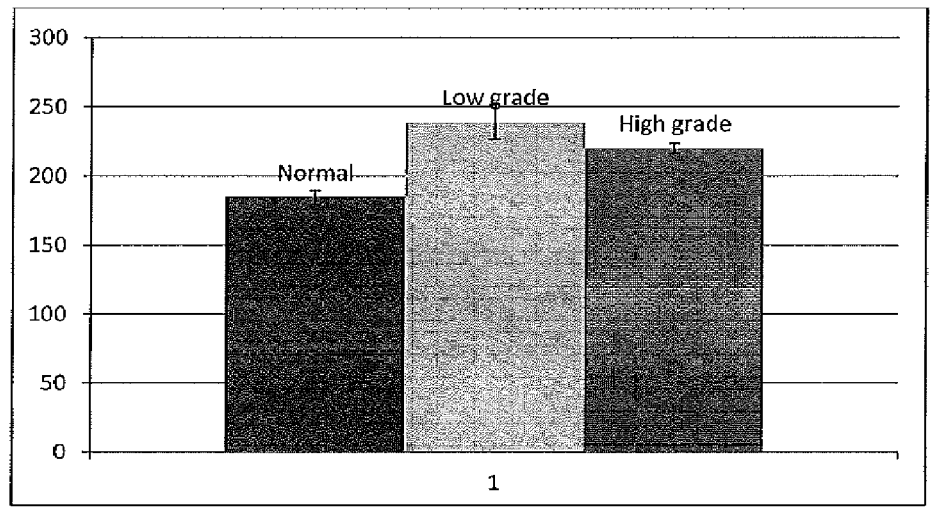
FIGS. 7A to 7F show graphical representations of the "control mean" (dark grey—left), "low grade glioma mean" (light grey—middle), and "high grade glioma mean" (medium grey—right) and also error bars, in relation to FGF, G-CSF, sHER2neu, sIL-6Ralpha, Prolactin, and sVEGFR1 respectively.
Figure 7B:
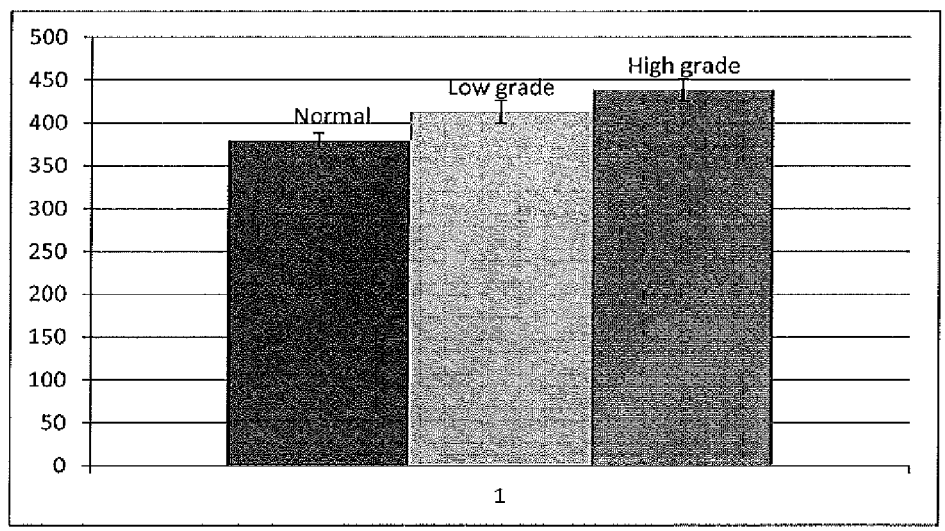
Figure 7C:
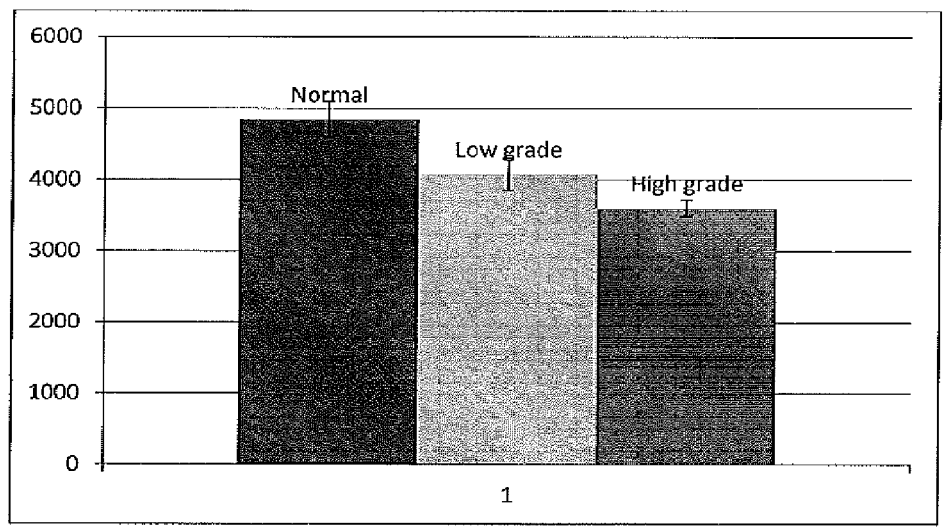
Figure 7D:
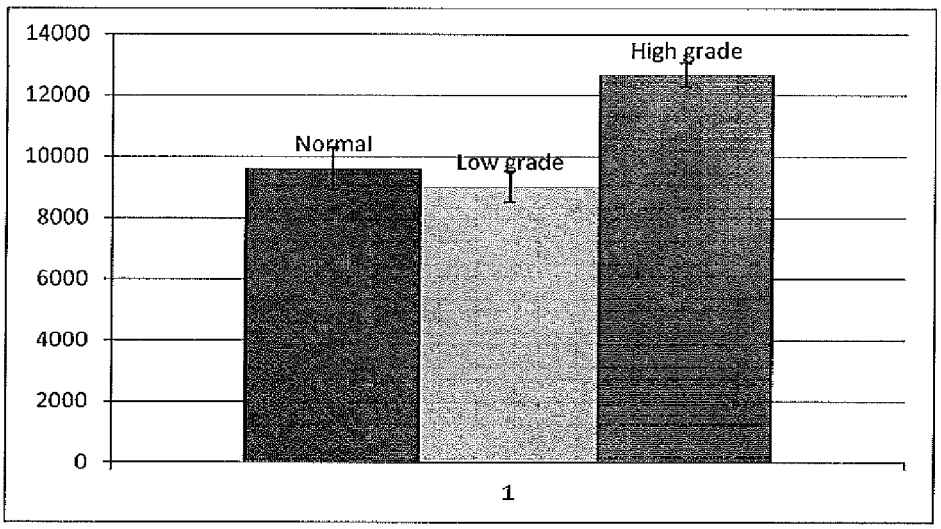
Figure 7E:
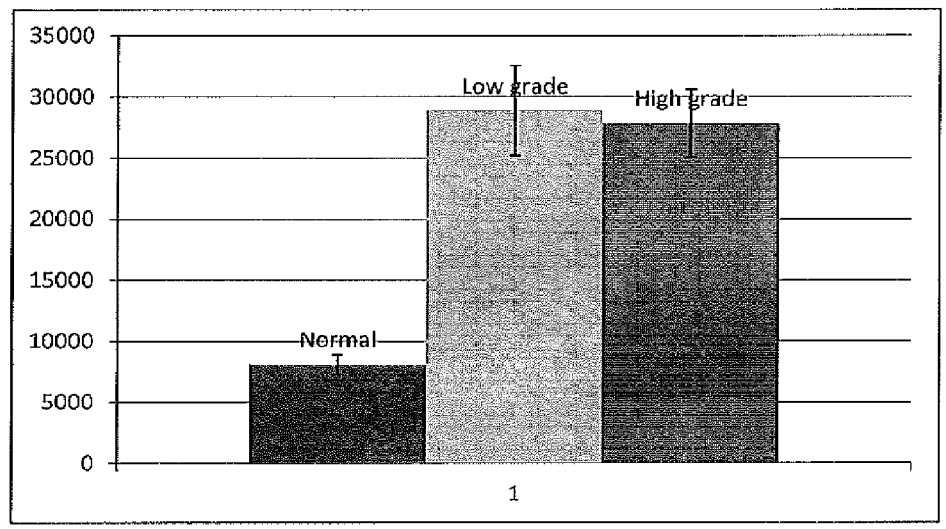
Figure 7F:
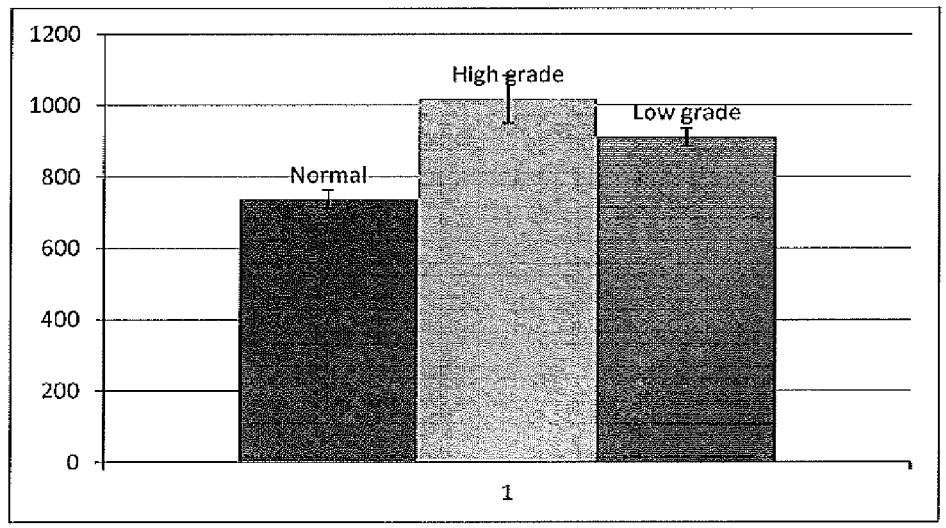

Unless otherwise stated, the following terms used in the specification and claims have the following meanings set out below.

Herein, "diagnosis" or "prognosis" generally includes a determination of the presence, the extent, the severity, and/or the aggressiveness of a brain cancer or proliferative disorder. As such, determining a favourable or unfavourable diagnosis or prognosis generally includes a determination of the presence, the extent, the severity, and/or the aggressiveness of a brain cancer or proliferative disorder. In a particular embodiment, a "diagnosis" or "prognosis" may refer to the mere presence of a brain cancer or proliferative disorder.

Herein, references to a "blood sample" include a sample of whole blood or a component thereof (e.g. blood serum or plasma).

Herein, "plasma" refers to the straw-colored/pale-yellow liquid component of blood that normally holds the blood cells in whole blood in suspension. It makes up about 55% of total blood volume. It is the intravascular fluid part of extracellular fluid (all body fluid outside of cells). It is mostly water (93% by volume) and contains dissolved proteins (major proteins are fibrinogens, globulins and albumins), glucose, clotting factors, mineral ions ($Na^+$, $Ca^{++}$, $Mg^{++}$, $HCO_3^-$ $Cl^-$ etc.), hormones and carbon dioxide (plasma being the main medium for excretory product transportation). It is to be noted that, for plasma samples, both EDTA plasma and citrate plasma are suitable, where as heparin plasma is less preferred, since this can absorb certain cytokines.

Herein, "serum" refers to the component that is neither a blood cell (serum does not contain white or red blood cells) nor a clotting factor; it is the blood plasma with the fibrinogens removed.

"Cytokines" are well known in the art as cell-signaling protein molecules that are secreted by numerous cells and are a category of signaling molecules used extensively in intercellular communication. Cytokines can be classified as proteins, peptides, or glycoproteins; the term "cytokine" encompasses a large and diverse family of regulators produced throughout the body by cells of diverse embryological origin. Some "cytokines" may also be considered "angiogenesis factors", and visa versa.

"Angiogenesis Factors" are well known in the art as angiogenic growth factors. In the context of the present invention, "cytokines" are generally considered collectively with "angiogenesis factors" given their combined service as biomarkers for proliferative disorders, as demonstrated in the Examples and throughout the specification.

Herein, references to an "assay" or "assaying" includes any form of analysis, including standard biological assays (e.g. bioassays, immunoassays, etc.) and even spectroscopic analyses. In particular embodiments, the assay does not relate to spectroscopic analyses.

As used herein, a "subject" refers to an animal, preferably a mammal. In preferred embodiments, the subject is a human subject. In other embodiments, the subject is a non-human mammal, including but are not limited to, dog, cat, horse, etc.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

As used herein, by "peptide" and "protein" can be used interchangeably and mean at least two covalently attached amino acids linked by a peptidyl bond. The term protein encompasses purified natural products, or products which may be produced partially or wholly using recombinant or synthetic techniques. The terms peptide and protein may refer to an aggregate of a protein such as a dimer or other multimer, a fusion protein, a protein variant, or derivative thereof. The term also includes modifications of the protein, for example, protein modified by glycosylation, acetylation, phosphorylation, pegylation, ubiquitination, and so forth. A protein may comprise amino acids not encoded by a nucleic acid codon.

By "protein modification" or "protein mutation" is meant an amino acid substitution, insertion, and/or deletion in a polypeptide sequence or an alteration to a moiety chemically linked to a protein. For example, a modification may be an altered carbohydrate or PEG structure attached to a protein. The proteins of the invention may include at least one such protein modification.

Conservative substitution: One or more amino acid substitutions (for example of 1, 2, 5 or 10 residues) for amino acid residues having similar biochemical properties. Typically, conservative substitutions have little to no impact on the activity of a resulting polypeptide. For example, a conservative substitution in a contact phase factor inhibitory peptide may be an amino acid substitution that does not substantially affect the ability of the peptide to inhibit a contact phase factor or combination thereof.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

In one embodiment, the substitutions are among Ala, Val Leu and Ile; among Ser and Thr; among Asp and Glu; among Asn and Gln; among Lys and Arg; and/or among Phe and Tyr.

Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

The term "modified protein" or "mutated protein" encompasses proteins having at least one substitution, insertion, and/or deletion of an amino acid. A modified or mutated protein may have 1, 2, 3, 4, 5, 6, 7, 8, 9 or 10 or more amino acid modifications (selected from substitutions, insertions, deletions and combinations thereof).

Functionally Equivalent: Having an equivalent function. In the context of a contact phase factor inhibitory peptide, functionally equivalent molecules include different molecules that retain the function of inhibiting the same contact phase factor(s). For example, functional equivalents can be provided by sequence alterations in contact phase factor inhibitory peptide, wherein the peptide with one or more sequence alterations retains the ability of the unaltered peptide to inhibit one or more contact phase factors.

Examples of sequence alterations include, but are not limited to, conservative substitutions, deletions, mutations, and insertions. In one example, a given polypeptide binds an active, and a functional equivalent is a polypeptide that binds the same active. Thus a functional equivalent includes peptides that have the same binding specificity as a polypeptide, and that can be used in place of the polypeptide. In one example a functional equivalent includes a polypeptide wherein the binding sequence is discontinuous, wherein the active binds a linear epitope.

Purified: The term purified does not require absolute purity; rather, it is intended as a relative term. Thus, for example, a purified peptide preparation is one in which the peptide or protein is more enriched than the peptide or protein is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide.

The invention relates to proteins and peptides (e.g. cytokines and/or angiogenesis factors) having an identity of at least 75%, at least 80%, at least 85%, at least 90%, at least 95% with a protein or peptide of the disclosure, e.g. 96% or more, 97% or more, 98% or more or 99% or more; such proteins may have the activity of the corresponding protein or peptide of the disclosure.

One of skill in the art will appreciate that these sequence identity ranges are provided for guidance only; it is possible that strongly significant homologs could be obtained that fall outside the ranges provided. An alternative (and not necessarily cumulative) indication that two amino acid sequences are substantially identical is that the polypeptide of the first sequence is immunologically cross reactive with the polypeptide of the second sequence.

Variants, fragments or fusion proteins: The disclosed proteins include variants, fragments, and fusions thereof.

General Methodology

The present invention provides a means to conveniently detect malignant tumours, especially cancerous brain tumours, merely by assaying/analysing blood (particularly blood serum). The inventors have made the surprising discovery that cytokines and/or angiogenesis factors in blood serum are indicative of the presence of brain cancers. The inventors have also discovered that, where samples are prepared with sufficient care, spectroscopic analysis of a blood sample from a subject can yield a signature that can be correlated, to a high degree of accuracy, with the presence, extent, severity, or aggressiveness of proliferative disorders, especially malignant tumours, in a subject.

As demonstrated in the Examples, the data provided herein support the notion that cytokines and/or angiogenesis factors in a blood sample can be indicative of brain cancers in the subject from which the blood sample was taken, especially indicative of brain cancers such as glioma. Moreover, the data provided herein support the notion that spectroscopic signatures of a blood sample can be used to provide a rapid diagnosis and/or prognosis of a proliferative in the subject from which the blood sample was taken. It is reasonable to contemplate that the diagnostic methods of the invention apply broadly to a variety of proliferative disorders, especially a variety of brain cancers. Furthermore, based on the discoveries outlined in this disclosure, diagnostic methods and kits may be readily generated, using routine workshop techniques known in the art, along with any associated diagnostic tools (e.g. software etc.).

The present invention provides a simple, reliable, and cost-effective point-of-care diagnostic method that requires minimal human resource or skill to operate, is non-time consuming, and which facilitates rapid determination of malignancy/benignity of tumours with a reasonably high degree of accuracy. For instance, the exemplified ATR-FTIR methods of diagnosis provide diagnostic results within 10 minutes, whilst the cytokine/angiogenesis factor assays afford diagnostic results within 5 hours. This is a considerable contribution to the art. It is envisaged that the cytokine/ angiogenesis assays could be used in conjunction with the spectroscopic analyses in provide fast and reliable diagnoses of proliferative disorders, especially brain cancers such as glioma.

The methods of the invention are useful for enabling a clinician to make decisions with regards to the best course of treatment for a subject who is suffering from cancer or is suspected of developing cancer. It is preferred that the diagnostic method is used to enable a clinician to decide how to treat a subject who is suffering from cancer. In addition, the methods are useful to a clinician because it allows him or her to monitor the efficacy of a putative treatment for cancer. Hence, diagnostic kits according to the invention are useful for providing prognostic information with regards a cancer patient's condition, such that the clinician can carry out a treatment. The kit can also be used to monitor the efficacy of a putative treatment for cancer. The method and the kit are therefore very useful for guiding a cancer treatment regime for the clinician, and to monitor the efficacy of such a treatment regime. Advantageously, the levels of cytokines and/or angiogenesis factors in blood may be used as a diagnostic and/or prognostic marker for a large variety of cancer conditions, but especially brain cancers such as gliomas. The methods of the invention are also applicable to pre-cancerous conditions and cancers caused by oncogenic viruses.

Proliferative Disorder

The proliferative disorder is suitably a cancer, suitably a cancer of the brain or spine, most suitably a brain cancer (and/or associated tumours). In a particular embodiment, the brain cancer is glioma.

The three main types of malignant glioma are astrocytomas, ependymomas and oligodendrogliomas. The diagnostic methods of the invention may apply to all these types of glioma. A tumour with a mixture of the histological features present in the main three is known as a mixed glioma, which the present invention may also serve to diagnose. The table below shows the sub-types of high grade and low-grade gliomas.

| General Tumour Grade | WHO Grade | Grade Sub-type |
|---|---|---|
| Low Grade | I | Pilocytic astrocytoma |
| | II | Oligodendroglioma |
| | II | Astrocytoma |
| High Grade | III | Anaplastic astrocytomas |
| | III | Oligodendrogliomas |
| | IV | Glioblastoma multiforme |

In a particular embodiment, the brain cancer is either a low grade or high grade glioma. In a particular embodiment, the brain cancer is any one of Pilocytic astrocytoma, Oligodendroglioma, Astrocytoma, Anaplastic astrocytomas, Oligodendrogliomas, Glioblastoma multiforme glioma sub-types.

In a particular embodiment, the brain cancer is a Grade III or Grade IV glioma.

Subjects (Patients)

The subject is suitably an animal, preferably a mammal. In preferred embodiments, the subject is a human subject. In other embodiments, the subject is a non-human mammal, including but are not limited to, dog, cat, horse, etc.

The subject suitably has or is suspected as having a brain cancer or proliferative disorder as defined herein. In a particular embodiment, the subject has or is suspected to have brain cancer (especially glioma).

The subject is suitably a glioblastoma or a gliosarcoma patient. In a particular embodiment, the subject is a glioblastoma patient.

Blood Sample

The blood sample is suitably obtained by first extracting blood from the relevant subject. The blood is then preferably further processed, suitably to obtain a component thereof (e.g. blood serum).

The blood sample (or component thereof) used in the methods of the present invention is suitably blood serum or blood plasma. In a particular embodiment, the blood sample is blood serum. In a particular embodiment, the blood serum is human serum.

Blood serum is suitably obtained, by methods well known in the art, from a blood sample of the relevant subject.

In a particular embodiment, the blood serum used is whole serum, most preferably whole human serum. Whole serum may be used directly in the relevant assay, especially in spectroscopic analysis. Alternatively the serum sample may be diluted according to the requirements of the spectroscope (e.g. sensitivity) and the homogeneity required of the sample being analysed.

In another embodiment, the blood serum used is centrifugally filtered serum which has molecules above a certain molecular weight removed therefrom. For instance, the blood serum may be centrifugally filtered to remove components having a molecular weight above 100 kDa (kilodaltans). In another embodiment, the blood serum may be centrifugally filtered to remove components having a molecular weight above 10 kDa. In another embodiment, the blood serum may be centrifugally filtered to remove component having a molecular weight above 3 kDa. Any or all of the abovementioned centrifugally filtered serums may be used directly in the relevant assay, especially in spectroscopic analysis. Alternatively the centrifugally filtered serum sample may be diluted according to the requirements of the spectroscope (e.g. sensitivity) and the homogeneity required of the sample being analysed.

Where the blood serum (suitably whole serum) is to be used in an immunoassay and/or spectroscopic analysis, the serum sample is suitably prepared by allowing an extracted blood sample to first clot, suitably at room temperature, suitably for between 25 minutes and 1 h 10 minutes. The serum is then suitably centrifuged or filtered to clear the sample of precipitate. Certrifuging is suitably performed at between 9000 and 20000 rpm, suitably between 10000 and 15000 rpm, suitably for 5-20 mins, suitably at 2-8° C. Filtering of serum samples suitably involves filtering through a 0.8/0.22 μm dual filter to prevent instrument clogging. The blood serum should then be either assayed immediately or otherwise aliquot and store serum samples in single use aliquots at −70° C. Before assaying, suitably the serum sample is diluted with an appropriate sample diluents. Suitably 1 volume of serum sample may diluted with 2-5 volumes of sample diluents, suitably with 3 volumes of sample diluents. Since physiological levels of VCAM-1 and ICAM-1 are typically found at much higher concentrations, sample dilutions of 1:100 are frequently required to achieve concentrations in the measurable range of the standard curve. As such, one may optionally dilute serum 1:50 or 1:100 as follows: 1) dilute serum 1:4 in sample diluent, and 2) dilute further 1:25 using standard diluents.

Cytokines and Angiogenesis Factors

The present invention may suitably involve detecting amounts of (or the presence of) one or more cytokines and/or angiogensis factors in a blood sample (or component thereof). As such, cytokines and/or angiogenesis factors may serve as analytes within the blood sample. The inventors' surprising discovery of a correlation between brain cancers in subjects and the amounts of cytokines and/or angiogenesis factors within their blood now enables diagnosis and/or prognosis of a number of brain cancers. The discovery that cytokines and/or angiogensis factors serve as biomarkers, within a subject's blood, for brain cancers (especially brain cancers such as glioma) is a major advance in the arena of medical diagnostics since it overcomes many of the problems associated with existing diagnostic methods and allows for the rapid delivery of diagnoses with regard to malignant tumours, such a malignant brain tumours.

Suitably the analytes (i.e. cytokines and/or angiogenesis factors) are predetermined. In preferred embodiments, the analytes are human cytokines and/or human angiogenesis factors.

In a particular embodiment of the present invention, the cytokine and/or angeiogenesis factor analytes include human cytokines and/or angeiogenesis factors selected from IL-1β, IL-1ra, IL-2, IL-4, IL-5, IL-6, IL-7, IL-8, IL-9, IL-10, IL-12 (p70), IL-13, IL-15, IL-17, Exotaxin, Basic FGF, G-CSF, GM-CSF, IFN-γ, IP-10, (MCAF), MIP-1α, MIP-1β, PDGF-BB, RANTES, TNF-α, VEGF, IL-1α, IL-2Rα, IL-3, IL-12 (p40), IL-16, IL-18, CTACK, GRO-α, HGF, ICAM-1, IFN-α2, LIF, MCP-3, M-CSF, MIF, MIG, β-NGF, SCF, SCGF-β, SDF-1α, TNF-β, TRAIL, VCAM-1, or selected from PDGF-AA, sHER2 neu, sIL-6R alpha, prolactin, sVEGFR1, IGFBP-1, IL-18, PAI-1, VEGF C; or mouse cytokines and/or angiogenesis factors selected from IL-1α, IL-1β, IL-2, IL-3, IL-4, IL-5, IL-6, IL-9, IL-10, IL-12 (p40), IL-12 (p70), IL-13, IL-17, Exotaxin, G-CSF, GM-CSF, IFN-γ, KC, MCP-1 (MCAF), MIP-1α, MIP-1β, RANTES, TNF-α, IL-15, IL-18, Basic FGF, LIF, M-CSF, MIG, MIP-2, PDGF-BB, VEGF.

In a particular embodiment of the present invention, the cytokine and/or angeiogenesis factor analytes include human cytokines and/or angeiogenesis factors selected from IL-1β, IL-1ra, IL-2, IL-4, IL-5, IL-6, IL-7, IL-8, IL-9, IL-10, IL-12 (p70), IL-13, IL-15, IL-17, Exotaxin, Basic FGF, G-CSF, GM-CSF, IFN-γ, IP-10, (MCAF), MIP-1α, MIP-1β, PDGF-BB, RANTES, TNF-α, VEGF, IL-1a, IL-2Ra, IL-3, IL-12 (p40), IL-16, IL-18, CTACK, GRO-α, HGF, ICAM-1, IFN-α2, LIF, MCP-3, M-CSF, MIF, MIG, β-NGF, SCF, SCGF-β, SDF-1α, TNF-β, TRAIL, and VCAM-1; or mouse cytokines and/or angiogenesis factors selected from IL-1α, IL-1β, IL-2, IL-3, IL-4, IL-5, IL-6, IL-9, IL-10, IL-12 (p40), IL-12 (p70), IL-13, IL-17, Exotaxin, G-CSF, GM-CSF, IFN-γ, KC, MCP-1 (MCAF), MIP-1α, MIP-1β, RANTES, TNF-α, IL-15, IL-18, Basic FGF, LIF, M-CSF, MIG, MIP-2, PDGF-BB, VEGF.

In a particular embodiment of the present invention, the cytokine and/or angeiogenesis factor analytes include human cytokines and/or angeiogenesis factors selected from IL-1β, IL-1ra, IL-2, IL-4, IL-5, IL-6, IL-7, IL-8, IL-9, IL-10, IL-12 (p70), IL-13, IL-15, IL-17, Exotaxin, Basic FGF, G-CSF, GM-CSF, IFN-γ, IP-10, (MCAF), MIP-1α, MIP-1β, PDGF-BB, RANTES, TNF-α, VEGF, IL-1α, IL-2Rα, IL-3, IL-12 (p40), IL-16, IL-18, CTACK, GRO-α, HGF, ICAM-1, IFN-α2, LIF, MCP-3, M-CSF, MIF, MIG, β-NGF, SCF, SCGF-β, SDF-1α, TNF-β, TRAIL, VCAM-1, or selected from PDGF-AA, sHER2 neu, sIL-6R alpha, prolactin, sVEGFR1, IGFBP-1, IL-18, PAI-1, VEGF C.

In a particular embodiment of the present invention, the cytokine and/or angeiogenesis factor analytes include human cytokines and/or angeiogenesis factors selected from IL-1β, IL-1ra, IL-2, IL-4, IL-5, IL-6, IL-7, IL-8, IL-9, IL-10, IL-12 (p70), IL-13, IL-15, IL-17, Exotaxin, Basic FGF, G-CSF, GM-CSF, IFN-γ, IP-10, (MCAF), MIP-1α, MIP-1β, PDGF-BB, RANTES, TNF-α, VEGF, IL-1α, IL-2Rα, IL-3, IL-12 (p40), IL-16, IL-18, CTACK, GRO-α, HGF, ICAM-1, IFN-α2, LIF, MCP-3, M-CSF, MIF, MIG, β-NGF, SCF, SCGF-β, SDF-1α, TNF-β, TRAIL, and VCAM-1.

In a particular embodiment of the present invention, the cytokine and/or angeiogenesis factor analytes include human cytokines and/or angiogenesis factors selected from IL-2, IL-4, IL-6, IL-8, IL-10, G-CSF, GM-CSF, IFN-γ, PDGF-BB, TNF-α, VEGF, HGF.

In a particular embodiment of the present invention, the cytokine and/or angeiogenesis factor analytes include human cytokines and/or angiogenesis factors selected from IL-8, IL-10, IFN-γ, PDGF-BB, HGF.

In a particular embodiment of the present invention, the cytokine and/or angeiogenesis factor analytes include human cytokines and/or angiogenesis factors selected from IL-8, IL-10, PDGF-BB, HGF.

In a particular embodiment of the present invention, the cytokine and/or angeiogenesis factor analytes include human cytokines and/or angiogenesis factors selected from IL-8, PDGF-BB, HGF.

In a particular embodiment of the present invention, the cytokine and/or angeiogenesis factor analytes include human cytokines and/or angiogenesis factors selected from IL-10, and PDGF-BB.

In a particular embodiment of the present invention, the angiogenesis factor analytes include angiogenesis factors (suitably human angiogenesis factors) selected follistatin, angiopoietin, leptin, and PECAM-1.

In a particular embodiment of the present invention, the angiogenesis factor analytes include angiogenesis factors (suitably human angiogenesis factors) selected follistatin, angiopoietin, and leptin.

In a particular embodiment of the present invention, the cytokine and angiogenesis factor analytes are selected from IL-2, IL-4, IL-6, IL-8, IL-10, GM-CSF, IFN-γ, PDGF-BB, TNF-α, VEGF, HGF, follistatin, angiopoietin, leptin, PECAM-1, or selected from PDGF-AA, sHER2 neu, sIL-6R alpha, prolactin, sVEGFR1, IGFBP-1, IL-18, PAI-1, VEGF C, G-CSF, FGF.

In a particular embodiment of the present invention, the cytokine and angiogenesis factor analytes are selected from IL-2, IL-4, IL-6, IL-8, IL-10, G-CSF, GM-CSF, IFN-γ, PDGF-BB, TNF-α, VEGF, HGF, follistatin, angiopoietin, leptin, and PECAM-1.

In a particular embodiment of the present invention, the cytokine and angiogenesis factor analytes are selected from IL-8, IL-10, IFN-γ, PDGF-BB, HGF, follistatin, angiopoietin, leptin, PECAM-1, or selected from PDGF-AA, sHER2 neu, sIL-6R alpha, prolactin, sVEGFR1, G-CSF, FGF.

In a particular embodiment of the present invention, the cytokine and angiogenesis factor analytes are selected from IL-8, IL-10, IFN-γ, PDGF-BB, HGF, follistatin, angiopoietin, leptin, and PECAM-1.

In a particular embodiment of the present invention, the cytokine and angiogenesis factor analytes are selected from IL-8, IL-10, PDGF-BB, HGF, follistatin, angiopoietin, leptin, PECAM-1, or selected from PDGF-AA, sHER2 neu, sIL-6R alpha, prolactin, sVEGFR1, G-CSF, FGF.

In a particular embodiment of the present invention, the cytokine and angiogenesis factor analytes are selected from IL-8, IL-10, PDGF-BB, HGF, follistatin, angiopoietin, leptin, and PECAM-1.

In a particular embodiment of the present invention, the cytokine and angiogenesis factor analytes are selected from IL-8, PDGF-BB, HGF, follistatin, angiopoietin, leptin, PECAM-1, or selected from PDGF-AA, sHER2 neu, sIL-6R alpha, prolactin, sVEGFR1, G-CSF, FGF.

In a particular embodiment of the present invention, the cytokine and angiogenesis factor analytes are selected from IL-8, PDGF-BB, HGF, follistatin, angiopoietin, leptin, and PECAM-1.

In a particular embodiment of the present invention, the cytokine and angiogenesis factor analytes are selected from IL-10, PDGF-BB, follistatin, angiopoietin, and leptin.

In a particular embodiment of the present invention, the cytokine and angiogenesis factor analyte(s) include follistatin.

Some cytokines may also be classed as angiogenesis factors, and visa versa. For instance, G-CSF, HGF, IL-8, PDGF-BB, VEGF, all of which are listed above under cytokines, may also be considered angiogenesis factors. There is thus a degree of overlap, which is why the inventors consider both cytokines and angiogenesis factors to be appropriate for use in the methods of the present invention. As such, in some embodiments, the one or more cytokines are selected from IL-2, IL-4, IL-6, IL-8, IL-10, GM-CSF, IFN-γ, TNF-α, and the one or more angiogenesis factors are selected from angiopoietin, follistatin, G-CSF, HGF, IL-8, leptin, PDGF-BB, PECAM-1, VEGF.

All the abovementioned abbreviations are outlined below. In any event, all of the abovementioned cytokines and angiogenesis factors are well known in the art without further elaboration, and are available commercially or in assay kits.

In preferred methods and diagnostic kits of the invention, between one and three cytokines and/or angiogenesis factors serve as the predetermined analytes in the methods.

Analysis of Blood Sample—Diagnosis/Prognosis

The methods of diagnosing and/or prognosing a brain cancer or proliferative disorder in a subject, as described herein, all involve analysis of a blood sample or a component thereof.

The methods of diagnosing and/or prognosing may suitably involve a preliminary step of obtaining a sample of whole blood (i.e. with plasma and cells) from the subject. The whole blood is then optionally further processed to isolate a component of the blood (e.g. blood serum or blood plasma) and/or remove unwanted material(s) (e.g. precipitates) from the blood or component thereof. Any further processing of the blood will depend on the method of analysis being used.

The methods of diagnosing and/or prognosing suitably involve correlating the analytical results/data associated with the assaying or analysis of the blood sample (or component thereof) with a favourable or unfavourable diagnosis and/or prognosis.

Correlating the analytical results with a favourable or unfavourable diagnosis and/or prognosis may be performed manually (e.g. by a clinician or other suitable analyst) or automatically (e.g. by computational means). Correlations may be established qualitatively (e.g. via a comparison of graphical traces or signatures) or quantitatively (e.g. by reference to predetermined threshold values or statistical limits). Correlating the analytical results may be performed using a predictive model, optionally as defined herein, which may have been developed by "training" a database of pre-correlated assays and/or analyses, In a particular embodiment, correlating the analytical results with a favourable or unfavourable diagnosis and/or prognosis involves an initial comparison of the analytical results with a reference standard or with previous analytic results that have already been correlated with a favourable or unfavourable diagnosis and/or prognosis (e.g. pre-correlated analytical results stored in a database). Correlations with previous analytical results may involve a statistical comparison or a "best fit" comparison (e.g. if comparing graphical traces with those stored in a database). The method of correlating the analytical results with a favourable or unfavourable diagnosis and/or prognosis may be a computer-implemented method of correlating. Suitably such computer-implemented methods incorporate predictive models, optionally in conjunction with appropriate databases.

Suitably, before correlating any analytical results, the analytical results are themselves validated. In particular, the analytical results should ideally be first validated as being definitive and without artefacts that can arise through variation in sample preparation and the like.

In particular embodiments, the methods relate to methods of diagnosing and not to methods of prognosing.

In another aspect of the invention, a plurality of methods of analysis or assaying upon a blood sample of a subject, according to the invention, are employed to diagnose and/or prognose a proliferative disorder in a subject. For instance the method of diagnosis may involve assaying a blood sample as defined herein and spectroscopically analysing a blood sample as defined herein. One method may be layered on top of the other. In some embodiments, the "assaying" methods may apply to any proliferative disorder (i.e. not only brain cancers) where they are used in combination with the "spectroscopic" analysis methods. As such, where these methods are used in conjunction with each other (whether in parallel or in series), any references herein to "assaying" methods in relation to brain cancers alone may be taken as relating to any proliferative disorders or brain cancers alone.

For the sake of clarity, in accordance with a further aspect of the invention, there is provided a method of diagnosing and/or prognosing a proliferative disorder in a subject, the method comprising:

assaying a blood sample (or a component thereof) of the subject in respect of one or more (suitably predesignated) cytokines and/or angiogenesis factors; and performing spectroscopic analysis upon a blood sample (or component thereof) of the subject to produce a spectroscopic signature characteristic of the blood sample (or component thereof).

Assaying a Blood Sample

Assaying the blood sample suitably involves determining the levels of one or more cytokines and/or angiogenesis factors within the blood sample. In a particular embodiment, the blood sample assayed is a blood serum sample. In another embodiment, the blood sample assayed is a blood plasma sample.

Optionally the levels (or concentrations) of the one or more cytokines and/or angiogenesis factors may be calibrated with or normalised relative to a standard marker whether said marker is intrinsic to the blood (i.e. a molecule which is typically present at substantially constant levels in the blood of all subjects) or is a substance added to the blood to give a known concentration of said substance within the blood, thus eliminating dilution effects on the analytical data.

The levels (or calibrated/normalised levels) of the one or more cytokines and/or angiogenesis factors may be assessed, for instance, against a predetermined threshold (e.g. determined by prior studies of cytokine/angiogenesis factor levels in blood samples of a representative cross-section of subjects with and without a brain cancer or proliferative disorder) for each of the one or more cytokines and/or angiogenesis factors or relative to each other (e.g.

comparing the relative levels/profile of the cytokines/angiogenesis factors concerned). Such an assessment may then be correlated with a diagnosis and/or prognosis. In particular, observation of elevated or reduced levels of each of the one or more cytokines and/or angiogenesis factors, whether relative to a predetermined threshold or relative to each other, may be correlated with a favourable or unfavourable diagnosis and/or prognosis. For instance, in a particular embodiment, a correlation with a favourable or unfavourable diagnosis and/or prognosis may be made by reference to one or more ratios between sets of specific cytokines and/or angiogenesis factors. In a particular embodiment, the ratio of the levels of PECAM-1 to PDGF-BB may be used to determine a favourable or unfavourable diagnosis and/or prognosis.

In a particular embodiment, the blood sample(s) are assayed with an immunoassay, for instance based on an antigen-antibody response.

Assaying the blood sample may involve any suitable assay known in the art. Each of the one or more cytokines and/or angiogenesis factors may be assayed for individually, optionally in series. As such, a blood sample may be split into multiple aliquots for testing. Alternatively, each of the one or more cytokines and/or angiogenesis factors may be assayed in parallel (e.g. as multiple aliquots). Alternatively, each of the one or more cytokines and/or angiogenesis factors may be assayed in parallel in the sample assay (i.e. with a single blood sample), for instance via a multiplex assay.

In a particular, the blood sample(s) are assayed using a magnetic bead-based multiplex assay designed to measure multiple cytokines and/or angiogenesis factors. The multiplexing feature makes it possible to quantitate the level of multiple proteins in a single well, in just 3 hrs, using as little as 12.5 µl of serum or plasma. Suitable assay kits include the Bio-Plex™ and Bio-Plex™ Pro systems, which incorporate magnetic beads into their design. The magnetic beads allow for the option of using magnetic separation during wash steps instead of vacuum filtration. Magnetic separation allows for greater automation without significant alterations to the standard Bio-Plex assay protocol. Standard Bio-Plex assay protocols are available online at www.bio-rad.com/bio-plex/, and are described in the Bio-Plex Pro™ Assay Handbook—http://www.bio-rad.com/webroot/web/pdf/lsr/literature/10014905.pdf.

The assay suitably employs a plurality of fluorescently dyed beads (e.g. xMAP technology) to simultaneously detect multiple cytokines and/or angiogenesis factors in a single assay (e.g. a single well). As such, two or more cytokines and/or angiogenesis factors may be the subject of analysis. In a particular embodiment, the up to 100 unique fluorescently dyed beads are used for cytokine/angiogenesis factor detection.

The assay suitably employs a flow cytometer with two lasers and associated optics to measure the different cytokines/angiogenesis factors bound to the surface of the beads.

The assay suitably employs a diagnostic kit with a (high-speed) digital signal processor that efficiently manages the fluorescent data.

The bead-based assays suitably operate in a manner similar to a capture sandwich immunoassay. For instance, an antibody directed against the desired cytokine and/or angiogenesis factor targets is suitably covalently bound to internally dyed beads. During the assay, the beads are suitably contacted with the relevant blood sample to facilitate reaction between the covalently bound antibody and the target cytokines and/or angiogenesis factors. After a sufficient contact time, the beads are suitably washed (optionally several times) to remove unbound protein. Thereafter, a biotinylated detection antibody specific to an epitope different from that of the capture antibody is suitably added to the bead reaction mixture. This suitably produces a sandwich of antibodies around the cytokine/angiogenesis factor target(s). A reporter complex (e.g. streptavidin-phycoerythrin (streptavidin-PE)) is then suitably added to bind to the biotinylated detection antibodies on the bead surface.

Data is suitably acquired from the bead reaction mixture using a suitable reader system. In a particular embodiment, the data is acquired using the Bio-Plex system (or Luminex system), a dual-laser, flow-based microplate reader system. The bead reaction mixture is suitably drawn up into the reader system. Lasers and associated optics suitably detect the internal fluorescence of the individual dyed beads as well as the fluorescent reporter signal on the bead surface. This suitably identifies each assay and reports the level of cytokine/angiogenesis factor target in the sample. Intensity of fluorescence detected on the beads indicates the relative quantity of target cytokines and/or angiogenesis factor molecules in the tested samples. A digital processor suitably manages the data output, which is suitably further analyzed and presented as fluorescence intensity (FI) and target concentration data, potentially using Bio-Plex Manager™ software.

The levels of the one or more cytokines and/or angiogenesis factors can then be used to determined a favourable or unfavourable diagnosis and/or prognosis, as described above, whether manually or automatically (i.e. through the data being directly processed by a computer as defined herein).

In some embodiments, assaying a blood sample (or a component thereof) of the subject in respect of one or more (suitably predesignated) cytokines and/or angiogenesis factors is performing spectroscopic analysis upon a blood sample (or component thereof) of the subject to produce a spectroscopic signature characteristic of the blood sample (or component thereof). It is envisaged that changes in the blood in respect of one or more (suitably predesignated) cytokines and/or angiogenesis factors can lead to changes in the relevant spectroscopic signatures.

Spectroscopic Analysis of a Blood Sample

Most suitably, the blood sample employed in spectroscopic analysis is blood serum or blood plasma, most preferably blood serum. The blood sample is preferably human blood serum.

The spectroscopic analysis may include any such analysis known in the art. For instance, spectroscopic analysis can include infra-red (IR), ultraviolet (UV), nuclear magnetic resonance (NMR), Raman, and many other viable forms of spectroscopy.

In preferred embodiments, however, the spectroscopic analysis is infra-red (IR) spectroscopic analysis. Suitably the IR spectroscopic analysis is fourier transform IR (FTIR) spectroscopic analysis, suitably employing at least 10 scans, suitably at least 15, suitably at least 30 scans. Suitably the FTIR spectroscopic analysis employs at most 100 scans, suitably at most 50 scans, and most suitably at most 40 scans. In preferred embodiments 32 scans are used. Suitably the scans are co-added. The number of scans is suitably selected to optimize data content and data-acquisition time.

Suitably IR spectra are collected in the region of 400-4000 wavenumbers ($cm^{-1}$). Suitably the IR spectra have a resolution of 10 $cm^{-1}$ or less, suitably 5 $cm^{-1}$ or less, especially 4 $cm^{-1}$. The spectroscopic signature characteristic of the blood sample (i.e. signature region) is suitably part or all of the relevant IR spectrum between 500 to 2500 cm$^{-1}$, more suitably part of all of the spectrum between 800 and 2000 cm$^{-1}$, and most suitably (all of) the spectrum between 900 and 1800 cm$^{-1}$.

Suitably, the spectroscopic analysis involves vector normalisation as a pre-processing step.

In preferred embodiments, the FTIR spectroscopic analysis is Attenuated Total Reflection FTIR (ATR-FTIR). This is a particularly effective form of spectroscopy for diagnosing and/or prognosing proliferative disorders from blood samples, owing to the high information content of the corresponding signatures arising from how the evanescent waves, inherent with such spectroscopic techniques, interact with the blood samples. ATR is a particular sampling technique enabling samples to be examined directly in the solid or liquid state. "ATR crystals" are suitably employed to support the blood sample during IR analysis. Suitably, the blood sample coats the surface (or part thereof) of the "ATR crystal" during IR analysis. Suitable ATR crystals include germanium, KRS-5 zinc selenide, diamond and silicon. The ATR crystals are suitably in a plate-like form. In a particular embodiment, the ATR crystal is a single reflection diamond crystal.

The blood sample is loaded onto an ATR crystal and, during ATR-FTIR analysis, IR light suitably travels through the ATR crystal, and reflects (suitably via total internal reflection) at least once off the internal surface in contact with the sample. Such reflection forms the "evanescent wave" which penetrates into the blood sample to an extent depending on the wavelength of light, the angle of incidence and the indices of refraction for the ATR crystal and the blood sample itself. Reflection numbers can be altered by varying the angle of incidence. Suitably the beam is ultimately received by an IR detector as it exits the crystal.

The "evanescent wave" effect only prevails if the ATR crystal is an optical material with a higher refractive index than the blood sample. As such, ATR-FTIR in the context of the present invention can be optimised by careful sample preparation.

A (relatively thin) film of the blood sample is suitably applied to the surface of the ATR crystal prior to FTIR analysis. The sample is suitably prepared so as to contain minimal or no trapped air. The blood sample film (or at least the part of it exposed to IR analysis) is suitably of (substantially) uniform thickness, suitably within a tolerance of +/−40 μm or less, more suitably within a tolerance of +/−20 μm or less, most suitably within a tolerance of +/−10 μm or less. The average film thickness of the blood sample across the surface of the ATR crystal (or at least the part of it exposed to IR analysis) is suitably between 0.1 and 200 μm, suitably between 1 and 100 μm, suitably between 2 and 50 μm. The maximum film thickness (i.e. the point of maximum thickness) of the blood sample across the surface of the ATR crystal (or at least the part of it exposed to IR analysis) is suitably between 1 and 200 μm, suitably between 2 and 100 μm, suitably between 5 and 50 μm, or suitably between 2 and 8 μm. The minimum film thickness (i.e. the point of minimal thickness) of the blood sample across the surface of the ATR crystal (or at least the part of it exposed to IR analysis) is suitably between 0 and 40 μm, suitably between 1 and 20 μm, suitably between 2 and 10 μm.

A blood sample film of appropriate thickness is suitably obtained by depositing 0.1-10 μL, suitably 0.2-5 μL most suitably 0.5-1.5 μL (or about 1 μL) of said blood sample upon the surface of an ATR crystal. Suitably the deposited blood sample is then allowed to dry to yield a blood sample film of an appropriate thickness. Suitably drying is effected at standard ambeint temperature and pressure (SATP) (i.e. about 25° C. at 100 kPa) for between 2 and 32 minutes, more suitably between 4 and 16 minutes, most suitably about 8 minutes, or other equivalent conditions yielding the same level of drying. Analysis of the resulting film via White Light Interferometry can indicate the thickness of the film across the surface of the ATR crystal, so as to verify the appropriate film thickness. The inventors have found that producing films of the appropriate thickness can reduce signature variance associated with sample preparation, such that any observed variance in signatures from blood sample to blood sample can be more reliably attributed to differential compositions rather than variability in sample preparation.

Suitably an individual aliquot taken from the bulk blood sample is used for each spectroscopic analysis. In this manner, further aliquots can be later used for further spectroscopic analyses on the sample blood sample, thereby assisting validation of results. Suitably, at least two spectroscopic analyses are performed on each blood sample. Moreover, suitably each individual spectroscopic analysis is repeated at least twice with the same aliquot, preferably at least three times, to help validate results.

The signature (in the signature region, typically 900-1800 cm$^{-1}$ in the case of ATR-FTIR spectroscopy) of the blood sample can then be correlated with a favourable or unfavourable diagnosis and/or prognosis, or be otherwise used to detect cancerous cells in a subject. Such a correlation is possible by comparing the signature with one or more pre-correlated signatures (i.e. signatures previously obtained and verified, e.g. via biopsies, as indicative of a favourable or unfavourable diagnosis and/or prognosis). This can be achieved by way of a qualitative assessment—e.g. certain signatures will resemble, perhaps to varying degrees, a signature characteristic of a blood sample of a subject with a proliferative disorder, whilst other signatures may differ to such signatures. As such, a qualitative assessment of the appearance of the signature may be used in the diagnosis and/or prognosis of a proliferative disorder. Such a qualitative assessment may be conducted manually, but is preferably conducted digitally via a computer running pursuant of computer software that performs such an assessment. Suitably any such computer software is able, from the assessment, to correlate the signature with a favourable or unfavourable diagnosis and/or prognosis.

Alternatively or additionally, correlation with a favourable or unfavourable diagnosis and/or prognosis may be made via a quantitative assessment—e.g. where the blood sample signature is compared to one or more reference signatures (already previously correlated with a favourable or unfavourable diagnosis and/or prognosis), optionally stored in a database, and suitably statistically analysed for a likelihood of a correlation.

In a particular embodiment, a spectroscopically obtained signature is compared to a plurality of pre-correlated signatures stored in a database (e.g. a "training set") in order to derive a correlation with a favourable or unfavourable diagnosis and/or prognosis. Statistical analysis (e.g. via pattern recognition algorithms) is suitably performed, preferably based on a comparison of the similarities and dissimilarities of the signature with the pre-correlated signatures, before the statistical analysis is used to correlate the signature with a favourable or unfavourable diagnosis and/or prognosis. Suitably pattern recognition algorithms include support vector machines (SVM) and principal component discriminant function analysis (PC-DFA).

In a particular embodiment, a spectroscopically obtained signature is correlated with a favourable or unfavourable diagnosis and/or prognosis based on a predictive model developed by "training" (e.g. via pattern recognition algorithms) a database of pre-correlated analyses.

Examination and/or comparison of blood sample signatures from spectroscopic analysis does not necessarily focus on particular peaks, or particular substances responsible for any particular peaks. However, in the case of ATR-FTIR, two amide peaks, which generally appear as a doublet of peaks at approximately 1550 $cm^{-1}$ and $1650^{-1}$ (especially when TSPA is used as an internal standard), appear to be important indicators of proliferative disorders since certain changes in these peaks indicate changes in protein structure suggestive of a proliferative disorder.

In a particular embodiment, the blood sample is whole serum.

In a particular embodiment, the blood sample is whole serum with components above 100 kDa removed by centrifugation filtration.

In a particular embodiment, the blood sample is whole serum with components above 10 kDa removed by centrifugation filtration.

In a particular embodiment, the blood sample is whole serum with components above 3 kDa removed by centrifugation filtration.

Any such centrifugal filtrations may be performed using a mini centrifuge combined with appropriate Protein filters at 14,000 rpm as per manufacturers instructions (Amicon membrane filters, Merck Millipore).

In some embodiments of the invention, a plurality of spectroscopic analyses are performed using a variety of serums (i.e. with differing degrees of filtration) derived from the same whole blood sample, and the results compared and/or used to cross-validate.

Databases, Computer Software, and Computer-Implemented Methods

The present invention provides a database comprising a plurality of data sets, each set pertaining to the amounts of one or more cytokines and/or angiogenesis in a particular blood sample (or component thereof) of a particular subject, each set being correlated with a favourable or unfavourable diagnosis and/or prognosis in relation to a brain cancer in said particular subject.

The present invention provides a database comprising a plurality of spectroscopic signatures, each signature pertaining to a particular blood sample (or component thereof) of a particular subject, each signature being correlated with a favourable or unfavourable diagnosis and/or prognosis in relation to a proliferative disorder in said particular subject.

The present invention provides a computer-readable medium (e.g. a disc) comprising a database as defined herein.

Databases of the present invention are suitably established by assaying or spectroscopically analysing a plurality of blood samples, from different subjects, to produce analytical data for each blood sample that is then systematically correlated with a favourable or unfavourable diagnosis and/or prognosis in relation to a proliferative disorder in the corresponding subject. Correlation of the analytical data with a favourable or unfavourable diagnosis and/or prognosis is suitably achieved by methods well known in the art, including biopsies. The analytical data may be further correlated with the degree of favourability or unfavourability of the diagnosis and/or prognosis (i.e. severity, agressiveness and/or extent of the proliferative disorder in question).

In the case of the database comprising a plurality of spectroscopic signatures, the database may be established through first acquiring plurality of blood sample signatures from a representative sample of subjects confirmed to have a/the proliferative disorder (or to have a proliferative disorder of a certain severity, agressiveness and/or extent) and a plurality of blood sample signatures from a representative sample of subjects confirmed not to have a/the proliferative disorder. Suitably the samples may also be matched for other criteria, such as sex or age, to facilitate normalisation of any variance between subjects otherwise correlated with the same proliferative disorder state.

A predictive model can be furthermore established from the database through "training" the data. Such a model may then be incorporated into computer software for future predictive purposes. The signatures may then be all combined and separated (optionally randomly or selectively) into a "training set" of signatures (preferably over 50%, suitably about 66% of the signatures are selected for the training set) and a "blind set" of signatures. The "training set" is then suitably trained using pattern recognition algorithms (e.g. using a support vector machine, such as those available through LIBSVM, or a PC-DFA), suitably by performing a grid search to optimise the cost and gamma functions to ensure that it can identify a training set, to thereby produce a viable predictive model. The "blind set" may then be offered to the model, which is then asked to predict whether the individual signatures in the blind set should correlate to a favourable or unfavourable diagnosis and/or prognosis. The predictions can then be translated into a "confusion matrix" illustrating which predictions were made. These predictions can then be validated (e.g. by verifying the actual result, e.g. from a biopsy) to calculate the sensitivity and specificity of the model.

The predictive model suitably has a sensitivity greater than 75%, more suitably greater than 80%, most suitably greater than 85%. The predictive model suitably has a specificity greater than 85%, suitably greater than 90%, more suitably greater than 98%.

Naturally, the model can be updated and refined as further results are obtained and correlated, and further criteria and variables are accounted for.

The model, once established, can be incorporated into diagnostic computer software. A computer running pursuant to the diagnostic computer software (and optionally also to the database) is then suitably configured by said software to perform predictive diagnoses and/or prognoses (suitably with the sensitivity and specificity established as above) upon newly inputed non-correlated signatures to thereby correlate said signatures with favourable or unfavourable diagnoses and/or prognoses.

As such, the present invention provides a computer installed with diagnostic computer software configured to operate the computer to perform a predictive diagnosis and/or prognosis in relation to a proliferative disorder based on a spectroscopic signature of a blood sample of a subject. Suitably, the diagnostic computer software incorporates a predictive model derived from one or more pattern recognition algorithms applied to a plurality of pre-correlated signatures. The computer may also be installed with a database, as defined herein, to help correlate results.

In a further aspect of the invention, there is provided a computer-readable medium containing diagnostic computer software as defined herein.

In a further aspect of the invention, there is provided a computer-implemented method of correlating the results of the assays or spectroscopic analysis as defined herein with a favourable or unfavourable diagnosis and/or prognosis, the method comprising:

collecting data from said assays or spectroscopic analysis;
   employing a predictive model, suitably based on pattern recognition algorithms conducted upon pre-correlated assays or spectroscopic analyses (optionally in conjunction with a database, as defined herein) to correlate said data with a favourable or unfavourable diagnosis and/or prognosis.

Diagnostic Kit

The present invention provides a diagnostic kit for diagnosing and/or prognosing a brain cancer in a subject, comprising a device configured to receive a blood sample (or component thereof) from the subject and assay the blood sample (or a component thereof) in respect of one or more (suitably predesignated) cytokines and/or angiogenesis factors; and a device (optionally the same as aforementioned) to correlate or facilitate correlation of the amounts of the one or more cytokines and/or angiogenesis factors within the blood sample (or component thereof) with a favourable or unfavourable diagnosis and/or prognosis.

The present invention provides a diagnostic kit for diagnosing and/or prognosing a proliferative disorder in a subject, comprising a device configured to receive a blood sample (or component thereof) from the subject and perform spectroscopic analysis upon the blood sample (or component thereof) of the subject to produce a spectroscopic signature characteristic of the blood sample (or component thereof); and a device (optionally the same as that aforementioned) to correlate or facilitate correlation of the spectroscopic signature of the blood sample (or component thereof) with a favourable or unfavourable diagnosis and/or prognosis.

In some embodiments, the device for assaying or analysing the blood sample is the same as the device for correlating or facilitating correlation of the results. The diagnostic kits of the invention may be a single integral device for receiving and assaying/analysing a sample and also correlating the results of said assay/analysis to a favourable or unfavourable diagnosis and/or prognosis.

In preferred embodiments, the device for correlating or facilitating correlation of the results is operable to perform a computer-implemented method of correlating as defined herein. Suitably the device for correlating or facilitating correlation of the results comprises a computer or is in communication with a computer (e.g. whether wired or wireless) configured with software to correlate said results with a favourable or unfavourable diagnosis and/or prognosis.

In the case of the diagnostic kit for spectroscopically analysing a blood sample, the correlating device suitably comprises or is in communication with a computer as defined herein, which computer is installed with diagnostic computer software configured to operate the computer to perform a predictive diagnosis and/or prognosis in relation to a proliferative disorder based on a spectroscopic signature of a blood sample of a subject.

In the case of the diagnostic kit for spectroscopically analysing a blood sample, the device configured to receive a blood sample may be configured to automatically prepare a blood sample (or component thereof) as described herein. For instance, in the case of ATR-FTIR, the device may be configure to automatically generate a film of the blood sample of the required thickness upon an ATR crystal prior to initiation of IR analysis. The device may comprises a film thickness verification facility (e.g. a white light interferometer) to verify the correct thickness of the blood sample upon the ATR crystal.

The diagnostic kits may be configured to automatically perform any of the method steps defined herein, optionally via a computer-implemented method.

EXAMPLES

Example 1

Assay of a Blood Sample

In the present example, cytokine and angiogenesis factor assays were performed upon blood plasma samples using the magnetic bead-based multiplex assays provided by a Bio-Plex Pro™ Assay kit. All the relevant protocols, which were duly followed in the present example, are set forth in the Instruction Manual entitled "Bio-Plex Pro™ Assays Cytokine, Chemokine, and Growth Factors Instruction Manual" available from Bio-Rad Laboratories, Inc at the website www.bio-rad.com, and in particular at http://www-.bio-rad.com/webroot/web/pdf/lsr/literature/10014905.pdf. The protocols of this Instruction Manual were followed in relation to "Bio-Plex Pro™ Human, Mouse, and Rat Cytokine Assays". The Bio-Plex™ system was prepared as described in the Instruction Manual, suitably calibrated, and validated as described. The magnetic beads present in the 96-well Bio-Plex Pro flat-bottom plates were washed via magnetic separation using the magnetic setting of the Bio-Plex Pro wash station. The 96-well Bio-Plex Pro flat-bottom plates were laid out appropriately, with wells assigned appropriately. Appropriate standards, supplied with the Bioplex system, were prepared in accordance with the Protocols set forth in the Instruction Manual.

As described in the Instruction Manual, The Bio-Plex™ suspension array system is built around the three core elements of xMAP technology:

Fluorescently dyed microspheres (also called beads), each with a distinct color code or spectral address to permit discrimination of individual tests within a multiplex suspension. This allows simultaneous detection of more than 100 different types of molecules in a single well of a 96-well microplate
   A dedicated flow cytometer with two lasers and associated optics to measure the different molecules bound to the surface of the beads
   A high-speed digital signal processor that efficiently manages the fluorescence data Bio-Plex Pro™ cytokine, chemokine, and growth factor assays are essentially immunoassays formatted on magnetic beads. The assay principle is similar to that of a sandwich ELISA (FIG. 1). Capture antibodies directed against the desired biomarker are covalently coupled to the beads. Coupled beads react with the sample containing the biomarker of interest. After a series of washes to remove unbound protein, a biotinylated detection antibody is added to create a sandwich complex. The final detection complex is formed with the addition of streptavidin-phycoerythrin (SA-PE) conjugate. Phycoerythrin serves as a fluorescent indicator, or reporter.

As also explained in the Instruction Manual, data from the reactions are acquired using a Bio-Plex system or similar Luminex-based reader. When a multiplex assay suspension is drawn into the Bio-Plex 200 reader for example, a red (635 nm) laser illuminates the fluorescent dyes within each bead to provide bead classification and thus assay identification. At the same time, a green (532 nm) laser excites PE to generate a reporter signal which is detected by a photomultiplier tube (PMT). A high-speed digital processor manages data output and Bio-Plex Manager™ software presents data as Median Fluorescence Intensity (MFI) as well as concentration (pg/mL). The concentration of analyte bound to each bead is proportional to the median fluorescence intensity (MFI) of reporter signal.

The Instruction Manual summarises the initial preparation for the assays as follows:

1. Plan the plate layout
2. Start up/warm up the Bio-Plex system (up to 30 min)
   Meanwhile, equilibrate assay reagents to room temperature (RT)
   Begin to thaw samples
3. Prime wash station or calibrate vacuum manifold
4. Calibrate the system (now, or later during an incubation)
5. Reconstitute a single vial of standards in 500 µl of the appropriate diluent, vortex and incubate on ice (30 min)
   For serum and plasma samples (as per the present example), use Bio-Plex standard diluent
6. Prepare the 8 point standard dilution series and blank.
   Add 72 µl diluent to tube S1, and 150 µl diluent to tubes S2-8 and blank.
   Transfer 128 µl reconstituted standard into S1
   Then serially dilute 4 fold from S1 thru S8 by transferring 50 µl between tubes. Vortex between transfers
7. Once thawed, prepare 1× samples
   Dilute serum, plasma and lysates in Bio-Plex sample diluent
8. Prepare 1× coupled beads in assay buffer, protect from light
   From 10× stock: Add 575 µl beads to 5,175 µl buffer
   From 20× stock: Add 288 µl beads to 5,472 µl buffer
9. Make sure samples and standards are at RT before dispensing The Instruction Manual summarises the running of the assays as follows:

1. Prewet filter plate with 100 µl assay buffer (skip for flat bottom)
2. Add 50 µl of 1× beads to the assay plate
3. Wash 2 times with 100 µl wash buffer
4. Add 50 µl samples, standards, blank, controls
5. Cover and incubate in the dark at RT with shaking at 300 RPM
   30 min—Human Group I,II and Mouse Group I,II
With 10 min remaining, prepare 1× Detection Ab in detection antibody diluent.
   From 10× stock: Add 300 µl Ab to 2,700 µl diluent
   From 20× stock: Add 150 µl Ab to 2,850 µl diluent
6. Wash 3 times with 100 µl wash buffer
7. Add 25 µl of detection antibody
8. Cover and incubate in the dark at RT with shaking at 300 RPM
   30 min—Human Group I,II; Mouse Group I,II
   Meanwhile, prepare software protocol; enter normalized standard S1 values
With 10 min remaining, prepare 1×SA-PE in assay buffer, From 100× stock:
   Add 60 µl SA-PE to 5,940 µl assay buffer. Protect from light
9. Wash 3 times with 100 µl wash buffer
10. Add 50 µl of strepavidin-PE
11. Cover and incubate in the dark at RT with shaking at 300 RPM
    10 min—Human Group I,II; Mouse Group I,II
12. Wash 3 times with 100 µl wash buffer
13. Resuspend beads in 125 µl assay buffer, shake at 1100 RPM for 30 sec
14. Read plate
    Low PMT (Low RP1)—Human group I,II; Mouse group I,II In accordance with the Instruction Manual, the reagents supplied with the Bio-Plex Pro™ assay kits for human, mouse, and rat cytokine assays include (Table 1):

TABLE 1

Reagents supplied with the Bio-Plex Pro ™ assay kits for human, mouse, and rat cytokine assays

| Contents | 1 × 96 Well Format | 10 × 96 Well Format |
|---|---|---|
| Universal Reagents and Diluents | | |
| Standard diluent* | 10 ml | 100 ml |
| Sample diluent* | 40 ml | 310 ml |
| Assay buffer | 50 ml | 500 ml |
| Wash buffer | 130 ml | 1,300 ml |
| Detection antibody diluent | 5 ml | 50 ml |
| Streptavidin-PE (100x) | 1 vial | 1 vial |
| Filter plate and/or flat bottom plate (96-well) | 1 plate | 10 plates |
| Sealing tape | 1 pack of 4 | 5 packs of 4 |
| Instruction manual | 1 | 1 |
| Human and Mouse Cytokine (Group I and II) | | |
| Coupled magnetic beads (10x) | 600 µl | 3,200 µl |
| Detection antibodies (10x) | 320 µl | 1,750 µl |
| Standard (additional vials sold separately) | 1 vial | 10 vials |
| Mouse Cytokine (Group III) and Rat Cytokine (Group I) | | |
| Coupled magnetic beads (20x) | 320 µl | 3,200 µl |
| Detaction antibodies (20x) | 175 µl | 1,750 µl |
| Standard (additional vials sold separately) | 1 vial | 1 vials |

*Bio-Plex Pro ™ high dilution reagent kit contains 70 ml serum-based diluent in lieu of standard diluent and sample diluent.

In accordance with the Instruction Manual, the testable cytokines include (Table 2):

TABLE 2 the testable cytokines

| | | | | | | | | |
|---|---|---|---|---|---|---|---|---|
| Human Cytokines | | | | Mouse Cytokines | | | Rat Cytokines | |
| Group I | Bead Region | Group II | Bead Region | Group I | Bead Region | Group II | Bead Region | Group I | Bead Region |
| IL-1β | 39 | IL-1α | 63 | IL-1α | 63 | IL-15 | 42 | IL-1α | 21 |
| IL-1ra | 25 | IL-2Rα | 13 | IL-1β | 19 | IL-18 | 20 | IL-1β | 28 |
| IL-2 | 38 | IL-3 | 64 | IL-2 | 36 | Basic FGF | 25 | IL-2 | 22 |
| IL-4 | 52 | IL-12(p40) | 28 | IL-3 | 18 | LIF | 45 | IL-4 | 33 |
| IL-5 | 33 | IL-16 | 27 | IL-4 | 39 | M-CSF | 26 | IL-5 | 52 |
| IL-6 | 19 | IL-18 | 42 | IL-5 | 52 | MIG | 44 | IL-6 | 56 |

TABLE 2-continued the testable cytokines

| Human Cytokines | | | | Mouse Cytokines | | | | Rat Cytokines | |
|---|---|---|---|---|---|---|---|---|---|
| Group I | Bead Region | Group II | Bead Region | Group I | Bead Region | Group II | Bead Region | Group I | Bead Region |
| IL-7 | 74 | CTACK | 72 | IL-6 | 38 | MIP-2 | 27 | IL-7 | 38 |
| IL-8 | 54 | GRO-α | 61 | IL-9 | 33 | PDGF-BB | 35 | IL-10 | 19 |
| IL-9 | 77 | HGF | 62 | IL-10 | 56 | VEGF | 47 | IL-12 (p40) | 76 |
| IL-10 | 56 | IFN-α2 | 20 | IL-12 (p40) | 76 | GROUP III | | IL-12 (p70) | 78 |
| IL-12 (p70) | 75 | LIF | 29 | IL-12 (p70) | 78 | IL-17F | 28 | IL-13 | 15 |
| IL-13 | 51 | MCP-3 | 26 | IL-13 | 37 | IL-21 | 14 | IL-17 | 72 |
| IL-15 | 73 | M-CSF | 67 | IL-17 | 72 | IL-22 | 15 | IL-18 | 20 |
| IL-17 | 76 | MIF | 35 | Eotaxin | 74 | IL-23p19 | 61 | EPO | 14 |
| Eotaxin | 43 | MIG | 14 | G-CSF | 64 | IL-31 | 29 | G-CSF | 64 |
| Basic FGF | 44 | β-NGF | 46 | GM-CSF | 73 | IL-33 | 13 | GM-CSF | 37 |
| G-CSF | 57 | SCF | 65 | IFN-γ | 34 | CD40L | 12 | GRO/KC | 57 |
| GM-CSf | 34 | SCGF-β | 78 | KC | 57 | MIP-3α | 30 | IFN-γ | 34 |
| IFN-γ | 21 | SDF-1α | 22 | MCP-1 | 51 | GROUP III | | M-CSF | 26 |
| IP-10 | 48 | TNF-α | 30 | MIP-1α | 77 | Singleplexes | | MIP-1α | 77 |
| MCP-1 | 53 | TRAIL | 66 | MIP-1β | 76 | IL-17E$_{(IL-25)}$ | 57 | MIP-2 | 27 |
| MIP-1α | 55 | GROUP II | | RANTES | 55 | IL-27p28 | 43 | MIP-3α | 36 |
| MIP-1β | 18 | Singleplexes | | TNF-α | 21 | ICAM-1 | 22 | RANTES | 55 |
| PDGF-BB | 47 | ICAM-1 | 12 | | | | | TNF-α | 43 |
| RANTES | 37 | VCAM-1 | 15 | | | | | VEGF | 47 |
| TNF-α | 36 | | | | | | | Eotaxin | * |
| VEGF | 45 | | | | | | | MCP-1 | * |

However, additional cytokines and angiogenesis factors were in fact tested, and the relevant standards and protocols developed accordingly. These additional cytokines and angiogenesis factors are detailed in the results section.

Whole Blood Sampling

Whole blood samples were collected from 50 glioma patients and 27 healthy subjects.

Preparation of Blood Plasma Samples from the Whole Blood Samples

Blood plasma samples for each of the 50 glioma patients and 27 healthy subjects were prepared by adding the corresponding fresh whole blood sample to a tube containing an anticoagulant, and spinning the tube at 13,200 rpm for 10 min at 4° C. until the blood cells fell to the bottom of the tube to clear the samples of precipitate. The blood plasma was then poured or drawn off. The resulting blood plasma had a density of approximately 1025 kg/m$^3$, or 1.025 kg/l. The blood plasma samples were then either assayed immediately or otherwise aliquoted and stored in single use aliquots at −70° C. for later use, though repeated freeze/thaw cycles were avoided.

Before conducting the assays, 1 volume of plasma sample was diluted with 3 volumes of sample diluents (for example, 50 μL sample+150 μL sample diluents).

Preparation of Coupled Beads

The preparation of coupled beads is now described using the protocols espoused in the Bio-Plex™ Pro instruction manual.

One tube of coupled beads is included with each kit. Instructions are provided for diluting the coupled beads to a 1× concentration.

When using 10-pack reagents, ensure that only the required volumes of coupled beads, detection antibodies, streptavidin-PE, and buffers have been removed from the tubes or bottles. For example, transfer a one-time volume of assay buffer, sufficient to perform all steps of the assay procedure (that is, prewetting the filter plate, diluting coupled beads, diluting streptavidin-PE, and resuspending the beads) into a 50 ml reservoir.

1. Use the Calculation Worksheet shown below to calculate the volume of coupled beads and assay buffer needed.
2. Add the required volume of assay buffer to a 15 ml polypropylene tube.
3. Vortex the coupled beads at mid speed for 30 sec. Carefully open the cap and pipet any liquid trapped in the cap back into the tube. This is important to ensure maximum bead recovery. Do not centrifuge the vial; doing so will cause the beads to pellet.
4. Pipet the required volume of stock coupled beads into the 15 ml tube containing assay buffer to dilute the coupled beads to a 1× concentration. Each well requires either 5 μl coupled beads (10×) or 2.5 μl coupled beads (20×) adjusted to a final volume of 50 μl using assay buffer. Refer to the example bead calculations in Tables 3-6 below, which include a 20% excess to compensate for transfer loss.

TABLE 3

Preparing 1× coupled beads from 10× stock. Premixed panel or one singleplex assay

| # of Wells | 10× Beads (μl) | Assay Buffer (μl) | Total Volume (μl) |
|---|---|---|---|
| 96 | 575 | 5,175 | 5,750 |
| 48 | 288 | 2,587 | 2,875 |

TABLE 4

Preparing 1× coupled beads from 10× stock. Mixing singleplex assays

| # of Wells | 10× Beads (μl), Singleplex #1 | 10× Beads (μl), Singleplex #2 | Assay Buffer (μl) | Total Volume (μl) |
|---|---|---|---|---|
| 96 | 575 | 575 | 4,600 | 5,750 |
| 48 | 288 | 288 | 2,300 | 2,876 |

TABLE 5

Preparing 1x coupled beads from 20x stock. Premixed panel or one singleplex assay.

| # of Wells | 20x Beads (μl) | Assay Buffer (μl) | Total Volume (μl) |
|---|---|---|---|
| 96 | 288 | 5,472 | 5,760 |
| 48 | 144 | 2,736 | 2,880 |

TABLE 6

Preparing 1x coupled beads from 20x stock. Mixing singleplex assays

| # of Wells | 20x Beads (μl), Singleplex #1 | 20x Beads (μl), Singleplex #2 | Assay Buffer (μl) | Total Volume (μl) |
|---|---|---|---|---|
| 96 | 288 | 288 | 5,184 | 5,760 |
| 48 | 144 | 144 | 2,592 | 2,880 |

5. Protect the beads from light with aluminum foil. Equilibrate at room temperature for 20 min prior to use.

Magnetic Bead-Based Multiplex Assay

The assays were then run as described in the Bio-Plex™ Pro instruction manual (as also set forth below).

Bring all buffers, diluted standards, diluted coupled beads, and samples to room temperature prior to use. To ensure optimal performance, pipet carefully (avoiding bubbles) with a calibrated pipet, and use new pipet tips.

Add Coupled Beads, Standards, and Samples and then:
1. Cover unused wells with sealing tape.
2. Prewet the filter plate.
3. Vortex the diluted coupled beads for 30 sec at medium speed.
   Pour the diluted coupled beads into a reagent reservoir and add 50 μl to each well.
   TIP: A multichannel pipet is highly recommended for ease of use and efficiency.
4. Wash the wells twice with the wash method of choice.
5. Gently vortex the diluted standards, blanks, samples, and controls (if applicable) for 1-3 sec. Add 50 μl diluted standard, control, or sample to each well, changing the pipet tip after every volume transfer.
6. Incubate on shaker at room temperature as specified in Table 7 below.

TABLE 7

Assay Incubation Times

| Assay | Incubation Time |
|---|---|
| Bio-Plex Pro human cytokine (group I and II) | 30 min |
| Bio-Plex Pro mouse cytokine (group I and II) | 30 min |
| Bio-Plex Pro mouse cytokine (group III) | 1 hr |
| Bio-Plex Pro rat cytokine (group I) | 1 hr |
| Bio-Plex Pro TGF-β | 2 hr |

NOTE:
Incubation times have been optimized for each assay and should not exceed 4 hr Be consistent with this incubation time for optimal reproducibility.

Prepare and Add Detection Antibodies.

One tube of detection antibodies is included with each kit. Instructions are provided for diluting the detection antibodies to a 1x concentration.
1. While the samples are incubating, use the Calculation Worksheet shown below to calculate the volume of detection antibodies and detection antibody diluent needed. Detection antibodies should be prepared 10-15 min before use.
2. Add the required volume of detection antibody diluent to a 15 ml tube.
3. Vortex the detection antibodies for 15-20 sec at medium speed, then perform a 30 sec spin to collect the entire volume at the bottom of the vial.
4. Pipet the required volume from each detection antibody tube into a 15 ml polypropylene tube. Each well of the assay requires either 2.5 μl detection antibody (10×) or 1.25 μl detection antibody (20×) adjusted to a final volume of 25 μl.

Refer to the example detection antibody calculations in Tables 8-11 below. These calculations include a 25% excess to compensate for transfer loss.

Tables 8-11 summarize the volumes required to prepare 1× detection antibodies from a single 10× or 20× stock. Also shown are volumes to prepare 1× antibodies when mixing two 10× or two 20× stocks. For instructions on preparing 1× antibodies from two stocks at different concentrations (for example when mixing human diabetes (20×) with human group I assays (10×), refer to the Bio-Plex Pro diabetes instruction manual (bulletin #10010747).

TABLE 8

Preparing 1x coupled beads from 10x stock. Premixed panel or one singleplex assay

| # of Wells | 10x Detection Antibodies (μl) | Detection Antibody Diluent (μl) | Total Volume (μl) |
|---|---|---|---|
| 96 | 300 | 2,700 | 3,000 |
| 48 | 150 | 1,350 | 1,500 |

TABLE 9

Preparing 1x coupled beads from 10x stock. Mixing singleplex assays

| # of Wells | 10x Detection Antibodies (μl), Singleplex #1 | 10x Detection Antibodies (μl), Singleplex #2 | Detection Antibody Diluent (μl) | Total Volume (μl) |
|---|---|---|---|---|
| 96 | 300 | 300 | 2,400 | 3,000 |
| 48 | 150 | 150 | 1,200 | 1,500 |

TABLE 10

Preparing 1x coupled beads from 20x stock. Premixed panel or one singleplex assay.

| # of Wells | 20x Detection Antibodies (μl) | Detection Antibody Diluent (μl) | Total Volume (μl) |
|---|---|---|---|
| 96 | 150 | 2,850 | 3,000 |
| 48 | 75 | 1,425 | 1,500 |

TABLE 11

Preparing 1x coupled beads from 20x stock. Mixing singleplex assays

| # of Wells | 20x Detection Antibodies (µl), Singleplex #1 | 20x Detection Antibodies (µl), Singleplex #2 | Detection Antibody Diluent (µl) | Total Volume (µl) |
|---|---|---|---|---|
| 96 | 150 | 150 | 2,700 | 3,000 |
| 48 | 75 | 75 | 1,350 | 1,500 |

5. After incubating the samples, slowly remove and discard the sealing tape.
6. Wash three times with the wash method of choice.
7. Vortex the diluted detection antibodies gently for 1-3 sec. Pour the diluted detection antibodies into a reagent reservoir and add 25 µl to each well using a multichannel pipet.
8. Cover the plate with a new sheet of sealing tape and seal the wells. Incubate on shaker at room temperature as specified in Table 12 below.

TABLE 12

Assay Incubation Times

| Assay | Incubation Time |
|---|---|
| Bio-Plex Pro human cytokine (group I and II) | 30 min |
| Bio-Plex Pro mouse cytokine (group I, II, III) | 30 min |
| Bio-Plex Pro rat cytokine (group I) | 30 min |
| Bio-Plex Pro TGF-β | 1 hr |

Prepare and Add Streptavidin-PE
1. While the detection antibodies are incubating, use the Calculation Worksheet shown below to calculate the volume of streptavidin-PE (100×) and assay buffer needed. Each well requires 0.5 µl streptavidin-PE (100×) adjusted to a final volume of 50 µl with assay buffer. Streptavidin-PE should be prepared 10 min before use.
2. Add the required volume of assay buffer to a 15 ml tube.
3. Vortex the streptavidin-PE tube for 15-20 sec at medium speed. Perform a 30 sec spin to collect the entire volume at the bottom of the vial.
4. Pipet the required volume of streptavidin-PE into a 15 ml polypropylene tube containing assay buffer to dilute the streptavidin-PE to a 1× concentration.
Table 13 below shows an example calculation to dilute streptavidin-PE, which includes a 25% excess to compensate for transfer loss. Protect the streptavidin-PE from light until ready to use.

TABLE 13

Preparing streptavidin-PE from 100x stock

| # of Wells | 100x Streptavidin-PE (µl) | Assay Buffer (µl) | Total Volume (µl) |
|---|---|---|---|
| 96 | 60 | 5,940 | 6,000 |
| 48 | 30 | 2,970 | 3,000 |

5. After detection antibody incubation, slowly remove and discard the sealing tape.
6. Wash three times with the wash method of choice.
7. Vortex the diluted streptavidin-PE at medium speed for 3-5 sec. Pour the diluted streptavidin-PE into a reagent reservoir and add 50 µl to each well using a multichannel pipet.
8. Incubate on shaker at room temperature for the specified time shown in Table 14 below.

TABLE 14

Assay Incubation Time

| Assay | Incubation Time |
|---|---|
| Bio-Plex Pro human cytokine (group I and II) | 10 min |
| Bio-Plex Pro mouse cytokine (group I, II, III) | 10 min |
| Bio-Plex Pro rat cytokine (group I) | 10 min |
| Bio-Plex Pro TGF-β | 30 min |

9. After the streptavidin-PE incubation step, slowly remove and discard the sealing tape.
10. Wash the wells three times with the wash method of choice.
11. Add 125 µl assay buffer to each well. Cover the plate with a new sheet of sealing tape. Shake the plate at room temperature at 1,100 rpm for 30 sec and slowly remove the sealing tape. Ensure that the plate cover has been removed before placing the plate on the reader.

Reading the Assay Plate

Assay plates were read in accordance with the Instruction Manual, as described below.

Bio-Plex Manager™ software is recommended for all Bio-Plex Pro assay data acquisition and analysis. Instructions for Luminex xPONENT software are also included. For instructions using other xMAP system software packages, contact Bio-Rad Technical Support or your regional Bio-Rad field applications specialist.

The protocol should be prepared in advance so that the plate is read as soon as the experiment is complete. A protocol file specifies the analytes used in the reading, the plate wells to be read, sample information, the values of standards and controls, and instrument settings.

Protocols may be obtained from within Bio-Plex Manager software version 6.0 or created from the File menu. Bio-Plex Manager software version 6.0 contains protocols for most Bio-Plex assays. The protocols should be chosen of new protocols should be created.

Protocols are prepared via the following steps:
1. Describe protocol and enter information about the assay.
2. Select analytes (from Table 2 above).
3. Format the plate according to the Plate Layout template created for the assay.
4. Enter details of the standards—e.g. highest concentration of each analyte, dilution factors, lot numbers, etc.
5. Enter controls information, including concentration and dilution information for each user-specified control for each assay.
6. Enter sample information, including the appropriate dilution factor.
7. Run the software protocols appropriate for the analytes concerned.

Data is acquired via the following steps:
1. Shaking the assay plate at 1,100 rpm for 30 sec, and visually inspecting plate to ensure that the assay wells are filled with buffer.
2. Run the protocol to start acquiring data.
3. Use the "wash between plates" function after each plate run to reduce clogging.

Data analysis and outlier removal is then performed.
Outliers are identified as standard data points that do not meet accuracy or precision requirements and should be considered invalid when performing curve fitting. As such, they should be removed to generate a more realistic and accurate standard curve. This may result in an extended assay working range and allow quantitation of samples that might otherwise be considered out of range (OOR).

In Bio-Plex Manager software version 6.0, outliers can be automatically removed by selecting the Optimize button in the Standard Curve window. In Bio-Plex Manager software 6.0 and earlier versions, outliers also can be manually selected in the Report Table.

Calculations

The Bio-Plex™ Pro instruction manual details the following calculations:

Plan Plate Layout

1. Fill out the 96-well plate template (page 43) as instructed in the Plan Plate Layout section (page 13).

If using either a premixed panel or one singleplex assay, follow these directions.

Enter the number of wells that will be used in the assay: _____ (1)

Calculations for Coupled Beads

1. Determine the volume of 1× coupled beads needed.
   a. Each well requires 50 μl of coupled beads (1×): _____ (1)×50 μl=_____ μl (2)
   b. Include a 20% excess to ensure enough volume: _____ μl (2)×0.20=_____ μl (3)
   c. Total volume of 1× coupled beads: _____ μl (2)+_____ μl (3)=_____ μl (4)
   d. Volume of 20× coupled beads stock: _____ μl (4)/20=_____ μl (5)
   e. Volume of assay buffer required: _____ μl (4)−_____ μl (5)=_____ (6)

Calculations for Coupled Beads

1. Determine the volume of 1× coupled beads needed.
   a. Each well requires 50 μl of coupled beads (1×): _____ (1)×50 μl=_____ μl (2)
   b. Include a 20% excess to ensure enough volume: _____ μl (2)×0.20=_____ μl (3)
   c. Total volume of 1× coupled beads: _____ μl (2)+_____ μl (3)=_____ μl (4)
   d. Volume of 20× coupled beads stock: _____ μl (4)/20=_____ μl (5)
   e. Volume of assay buffer required: _____ μl (4)−_____ μl (5)=_____ (6)

Calculations for Coupled Beads

1. Determine the volume of 1× coupled beads needed.
   a. Each well requires 50 μl of coupled beads (1×): _____ (1)×50 μl=_____ μl (2)
   b. Include a 20% excess to ensure enough volume: _____ μl (2)×0.20=_____ μl (3)
   c. Total volume of 1× coupled beads: _____ μl (2)+_____ μl (3)=_____ μl (4)
   d. Volume of 20× coupled beads stock: _____ μl (4)/20=_____ μl (5)
   e. Volume of assay buffer required: _____ μl (4)−_____ μl (5)=_____ (6)

If mixing singleplex assays, follow these directions.

Calculations for Coupled Beads

1. Determine the volume of 1× coupled beads needed.
   a. Each well requires 50 μl coupled beads (1×): _____ (1)×50 μl=_____ μl (2)
   b. Include 20% excess to ensure enough volume: _____ μl (2)×0.20=_____ μl (3)
   c. Total volume of 1× coupled beads: _____ μl (2)+_____ μl (3)=_____ μl (4)
   d. Enter the number of diabetes single set (or analytes) tubes that will be multiplexed=_____ (5)
   e. Volume of 20× coupled beads required from each coupled beads tube: _____ μl (4)/20=_____ μl (6)
   f. Total volume of diabetes bead stock required: _____ (5)×_____ μl (6)=_____ μl (7)
   g. Volume of assay buffer required: _____ μl (4)−_____ μl (7)=_____ μl (8)

Calculations for Detection Antibodies

2. Determine the volume of 1× detection antibody needed.
   a. Each well requires 25 μl detection antibodies (1×): _____ (1)×25 μl=_____ μl (9)
   b. Include a 25% excess to ensure enough volume: _____ μl (9)×0.25=_____ μl (10)
   c. Total volume of 1× detection antibodies: _____ μl (9)+_____ μl (10)=_____ μl (11)
   d. Enter the number of diabetes single set (or analytes) tubes that will be multiplexed=_____ (5)
   e. Volume of 20× detection antibodies required from each detection antibody tube: _____ μl (11)/20=_____ μl (12)
   f. Total volume of diabetes detection antibody stock: _____ μl (12)×_____ (5)=_____ μl (13)
   g. Volume of detection antibody diluent required: _____ μl (11)−_____ μl (13)=_____ μl (14)

Calculations for Streptavidin-PE

3. Determine the volume of 1× streptavidin-PE needed.
   a. Each well requires 50 μl streptavidin-PE (1×): _____ (1)×50 μl=_____ μl (15)
   b. Include 25% excess to ensure enough volume: _____ μl (15)×0.25=_____ μl (16)
   c. Total volume of 100× streptavidin-PE: _____ μl (15)+_____ μl (16)=_____ μl (17)
   d. Volume of 100× streptavidin-PE required: _____ μl (17)/100=_____ μl (18)
   e. Volume of assay buffer required: _____ μl (17) _____ μl (18)=_____ μ(19)

Processing of Data

The blood plasma samples from the 50 glioma patients and 27 healthy subjects were all assayed against various cytokines and angiogensis factors, and the levels of said cytokines and angiogensis factors determined in each case. A mean value for the cytokine and angiogensis factor levels for the 50 glioma patients ("Glioma Mean") and a mean value for the cytokine and angiogensis factor levels for the 27 healthy subjects ("Control Mean") was produced for each respective cytokine and angiogensis factor that was assayed, and the results compared. A statistical comparison was then made as to the significance of the particular cytokine and angiogensis factor in relation to its capacity to indicate the presence of gliomas.

FIGS. 1 to 7 show a graphical representation of the "control mean" (light grey) and "glioma mean" (dark grey), and also error bars, in relation to IL-8, Angiopoietin, Follistatin, HGF, Leptin, PDGF-BB, and PECAM-1 respectively.

FIGS. 7A to 7F show graphical representations of the "control mean" (dark grey—left), "low grade glioma mean" (light grey—middle), and "high grade glioma mean" (medium grey—right) and also error bars, in relation to FGF, G-CSF, sHER2neu, sIL-6Ralpha, Prolactin, and sVEGFR1 respectively. These figures demonstrate the applicability of the present invention to both low and high grade cancers.

Figure 8:
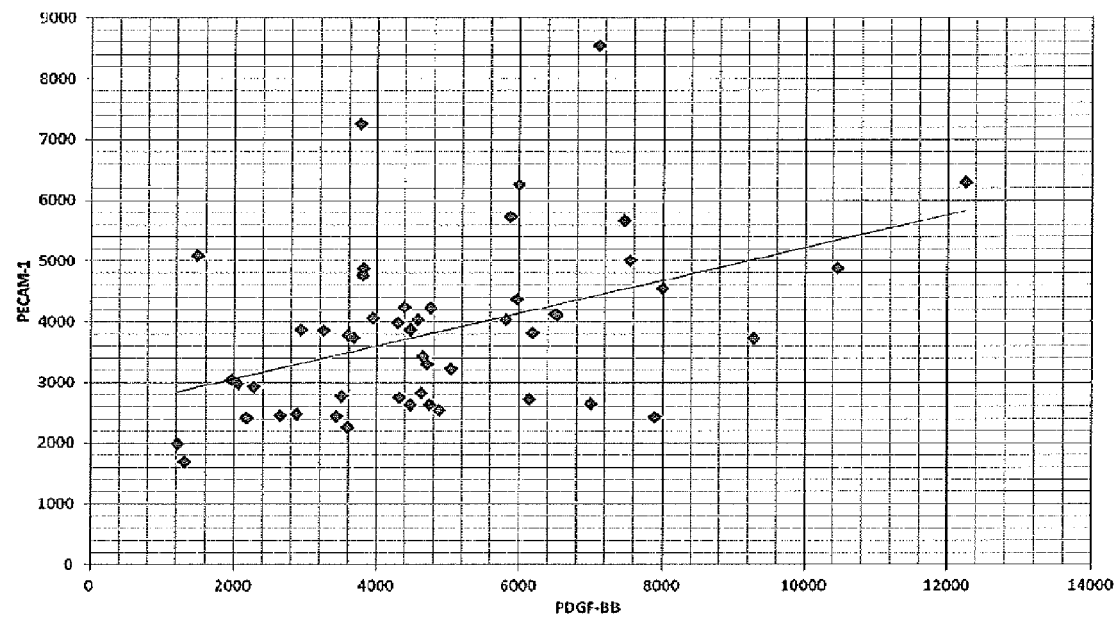
FIG. 8 is a scatter-graphical correlation chart for PECAM-1 and PDGF-BB showing the relationship between PECAM-1 and PDGF-BB levels in the 50 glioma patients, and demonstrating a degree of linearity and a correlation coefficient of 0.45.
Figure 8A:
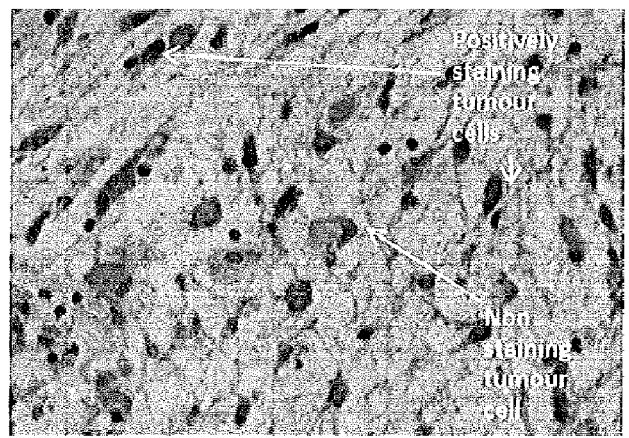
FIGS. 8A-8G shows photographic immunohistochemical comparisons between glioma and non-cancerous brain tissues, namely: a) glioma tumour section ×40 magnification showing positively staining and non-staining tumour cells; b) glioma tumour section ×40 magnification showing negatively staining blood vessels; c) non-cancerous brain tissue ×40 magnification showing negatively staining blood vessel; d) glioma tumour section ×40 magnification showing interstitial staining; e) glioma tumour section ×40 magnification showing interstitial staining, particularly of axonal tracts; f) non-cancerous brain tissue ×40 magnification showing negatively staining blood vessel; g) choroid plexus tissue showing positive cytoplasmic staining.
Figure 8B:
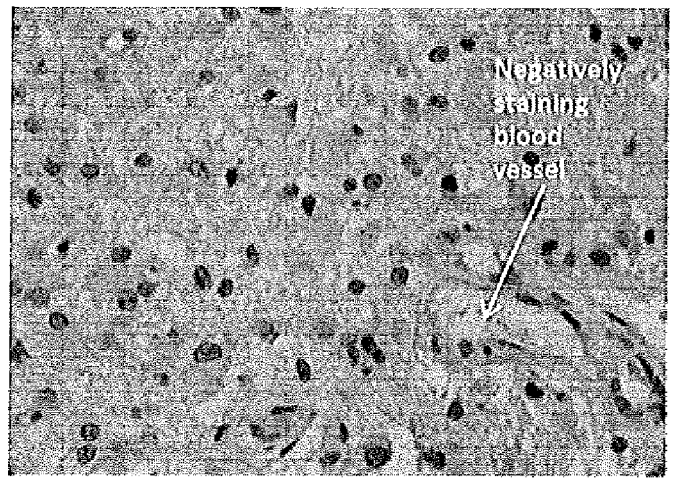
Figure 8C:
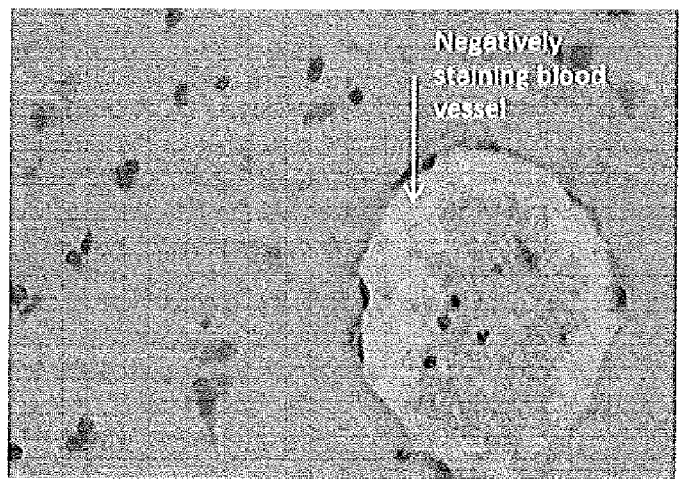
Figure 8D:
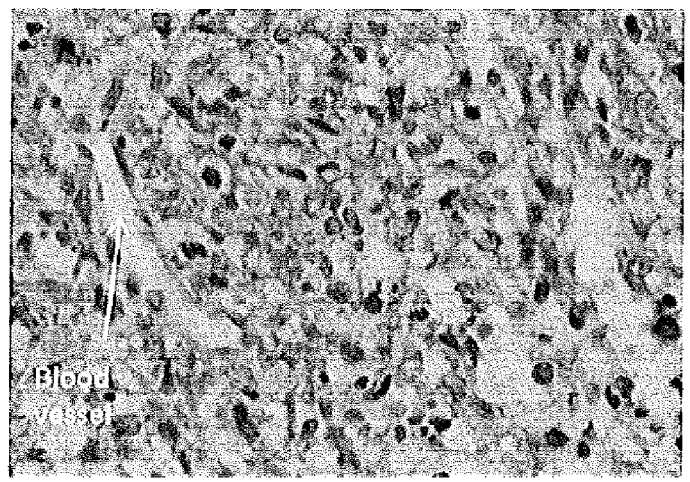
Figure 8E:
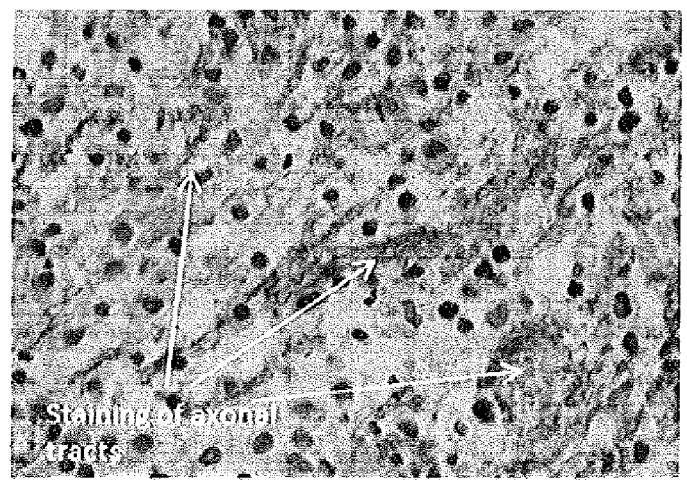
Figure 8F:
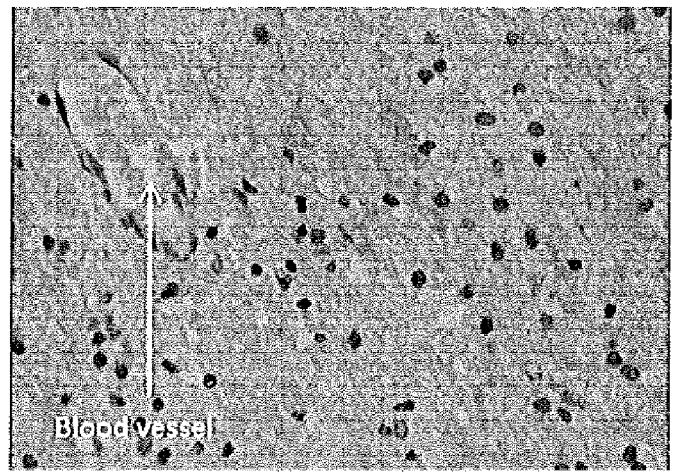
Figure 8G:
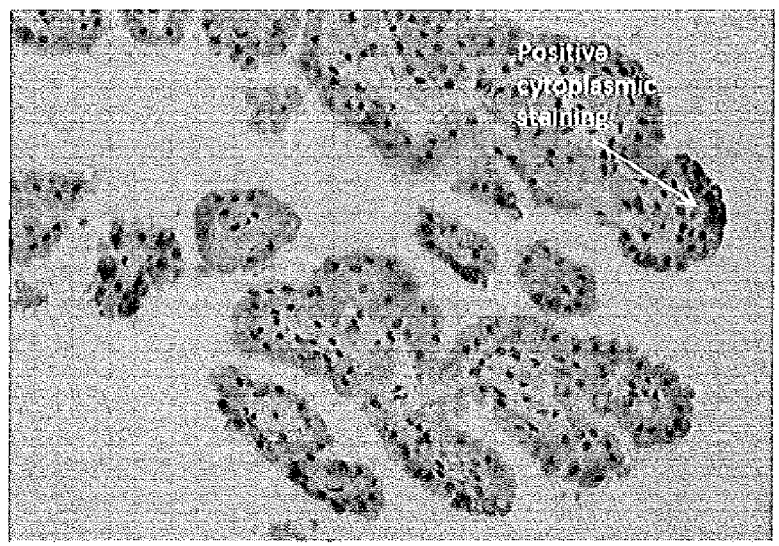

FIG. 8 is a scatter-graphical correlation chart for PECAM-1 and PDGF-BB showing the relationship between PECAM-1 and PDGF-BB levels in the 50 glioma patients, and demonstrating a degree of linearity and a correlation coefficient of 0.45. This suggests that considering the relative levels of both PECAM-1 and PDGF-BB may provide a good correlation with a favourable or unfavourable diagnosis in relation to glioma. It is also reasonable to consider relative levels or ratios between other sets of cytokines and/or angiogenesis factors as indicative of a favourable or unfavourable diagnosis in relation to glioma, or indeed in relation to other brain cancers.

Results

Table 15 below compares the "control mean" concentrations of each assayed cytokine and angiogensis factor with the "glioma mean" concentrations of each assayed cytokine and angiogensis factor, and reports the "significance" of the particular cytokine or angiogensis factor in question (i.e. whether or not said cytokine or angiogensis factor is a suitable biomarker in blood plasma for glioma).

TABLE 15

Comparison of "Control Mean" and "Glioma Mean" to determine Significance as a Biomarker for Glioma

| Cytokine/Angiogenesis factor | Control mean pg/ml | Glioma mean pg/ml | Significance ($P < 0.05$) |
|---|---|---|---|
| IL-2 | 2.060434783 | 2.113 | No |
| IL-4 | 0.204 | 0.225 | No |
| IL-6 | 3.730625 | 2.6252 | No |
| IL-10 | 3.113478 | 5.4772 | No |
| GM-CSF | 0 | 0.8078 | No |
| IFN-γ | 7.797391 | 1.93551 | YES |
| TNF-α | 8.53826087 | 8.5034 | No |
| Angiopoietin | 282.3258 | 195.1382 | YES |
| Follistatin | 407.9671 | 757.4796 | YES |
| HGF | 915.6583 | 1073.045 | YES |
| IL-8 | 20.13348 | 16.37449 | YES |
| Leptin | 5452.401 | 9102.635 | YES |
| PDGF-BB | 2817.792 | 4866.84 | YES |
| PECAM-1 | 2734.137 | 3832.264 | YES |
| VEGF | 64.29167 | 69.3364 | No |
| FGF | 184.6 | 220.2 | Yes |
| G-CSF | 379.4 | 438.4 | Yes |
| sHER2neu | 4845.3 | 3604.8 | Yes |
| sIL-6Ralpha | 9603.1 | 12672.6 | Yes |
| Prolactin | 8101.9 | 27827.7 | Yes |
| sVEGFR1 | 736.6 | 911 | Yes |
| PDGF AA | 7315 | 8578 | Yes |

As will be apparent, at least IFN-γ, Angiopoietin, Follistatin, HGF, IL-8, Leptin, PDGF-BB, PECAM-1, PDGF-AA, sHER2 neu, sIL-6R alpha, prolactin, sVEGFR1, G-CSF, and FGF show a high degree of "significance", though the significance of IFN-γ was treated with caution given that many individuals demonstrated a zero concentration of this particular cytokine. In addition, it was observed that levels of Follistatin are higher in glioma patients than healthy subjects, Interleukin 10 is higher, Angiopoetin is lower, Leptin is higher, and PDGF-BB are higher. These cytokines and angiogenesis factors are therefore clearly excellent candidates as blood plasma biomarkers of gliomas, and it is reasonable to presume that many other cytokines and/or angiogenesis factors may also possess excellent biomarker properties in this regard. Moreover, it is reasonable to conclude that other forms of brain cancer would also be detectable by reference to cytokine and/or angiogenesis factor biomarkers.

In view of the above disclosure, relevant diagnostic kits and methods can be readily developed, using routine workshop techniques known in the art.

The above data is further corroborated by immunohistochemical comparisons between glioma brain tissue and non-cancerous brain tissue. FIGS. 8A-8G shows photographic immunohistochemical comparisons between glioma and non-cancerous brain tissues, namely: a) glioma tumour section ×40 magnification showing positively staining and non-staining tumour cells; b) glioma tumour section ×40 magnification showing negatively staining blood vessels; c) non-cancerous brain tissue ×40 magnification showing negatively staining blood vessel; d) glioma tumour section ×40 magnification showing interstitial staining; e) glioma tumour section ×40 magnification showing interstitial staining, particularly of axonal tracts; f) non-cancerous brain tissue ×40 magnification showing negatively staining blood vessel; g) choroid plexus tissue showing positive cytoplasmic staining.

FIGS. 8A-8G show, in particular, immunohistochemical staining of Follistatin, thereby showing an increased accumulation of this protein in the brain tissue of glioma patients.

FIGS. 8A-8G show the ability of Follistatin to identify tumour margins during immunohistochemical staining of brain tissue. Some gliomas exhibited significant follistatin immunostaining of tumour cells, many appeared to express gemistocytic morphology. However staining was not uniform throughout the tumour sample and some cells were patently immuno-negative (FIG. a). Positive immunostaining was entirely cytoplasmic with no membrane or nuclear component and other tissue elements within the sections, including blood vessels, were completely negative (FIG. b). There were no specific features of the tumours or constituent cells which were evidently predictive of immunopositivity or to account for the significant variability between individual tumours. The non cancerous (viz. normal) brain tissue was uniformly negative throughout and there was no staining of either neurones or glial cells (FIG. c). There was a distinct interstitial stain in the presence of negatively staining cells that followed the axonal tracts of the sections (FIGS. d and e). There was no specific axonal staining and some of the axonal tracts did not take up any stain. The non-cancerous brain axonal tracts were uniformly negative (FIG. f). There was some specific cytoplasmic staining of some cells from the choroid plexus (FIG. g). This may suggest that Follistatin is being secreted into the CSF.

Example 2

Spectroscopic Analysis of a Blood Sample

In the present example, spectroscopic analyses were performed upon blood serum samples using the Attenuated Total Reflection Fourier Transform Infra-Red Spectroscopy (ATR-FTIR).

A JASCO FTIR-410—Specac Golden Gate™ spectrometer was used to perform the spectroscopic experiments, and the infra-red spectrum of blood serum samples were scanned of 400-4000 $cm^{-1}$ at at resolution of 4 $cm^{-1}$ using 32 scans that we then co-added.

Whole Blood Sampling

Whole blood samples were collected from 74 subjects in all, including 49 Grade IV gliomblastoma patients, and 25 healthy subjects. Where possible, the samples were age and sex matched.

Preparation of Blood Serum Samples from the Whole Blood Samples

Blood serum samples for each of the 74 subjects were prepared by allowing a fresh sample of whole blood to first clot at room temperature (25° C.) for 30 to 45 minutes before performing centrifugation at 13,200 rpm (or 1000-2000×g) for 10 min in a refrigerated centrigfuge at 4° C. to clear the sample of precipitate. The resulting supernatant liquid was serum. Following centrifugation, it was crucial to immediately transfer the serum to a clean polypropylene tube via a Pasteur pipette or such like. The samples were kept at 2-8° C. while handling and then apportioned into aliquots, stored, and transported at −20° C. or lower. Freeze-thaw cycles were avoided.

In the present example, the serum sample in relation to the abovementioned patients and healthy subjects were provided by the Brain Tumour North West Biobank. Four serum fractions were prepared and analysed. The following fractions ("serum types 1-4") were prepared:
1) Whole serum—directly as supplied.
2) Serum with components above 100 kDa removed by centrifugation filtration.
3) Serum with components above 10 kDa removed by centrifugation filtration.
4) Serum with components above 3 kDa removed by centrifugation filtration.

Centrifugation was performed using a mini centrifuge combined with appropriate Protein filters at 14,000 rpm as per manufacturers instructions (Amicon membrane filters, Merck Millipore).

Loading Sample onto ATR Crystal

For each of serum samples 1-4, 1 µL micro litre of serum was place onto the element (i.e. ATR crystal) of the ATR-FTIR accessory and left to dry for 8 minutes at room temperature. This has been shown to be a reproducible drying time for 1 micro litre of serum.

Figure 9:
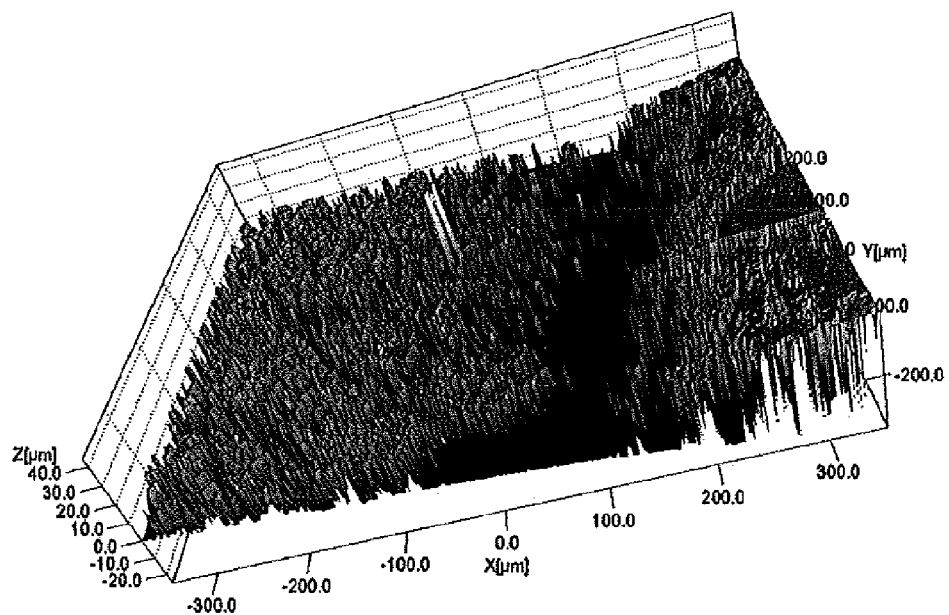
FIG. 9 shows a white light interferometric profile of the film of serum sample 1 (whole serum).

FIG. 9 shows a white light interferometric profile of the film of serum sample 1 (i.e. whole serum) which was deposited and dried in accordance with the above protocol. The thickness across the ATR crystal fluctuates between 0 and 40 microns in thickness. This is found to be an ideal thickness for the ATR-FTIR analysis of whole serum.

Figure 10:
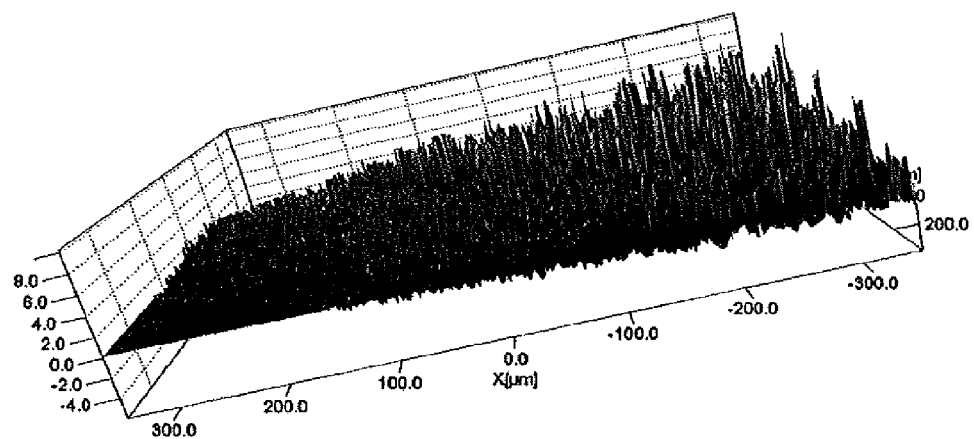
FIG. 10 shows a white light interferometric profile of the film of serum sample 3 (serum with components above 10 kDa removed).

FIG. 10 shows a white light interferometric profile of the film of serum sample 3 (serum with components above 10 kDa removed) which was deposited and dried according to the above protocol. The thickness across the ATR crystal fluctuates between 0 and 8 microns in thickness. This is found to be an ideal thickness for the ATR-FTIR analysis of whole serum.

The above described sample preparation process and subsequently described analysis was performed twice for each blood serum sample in order to validate results.

Various additional side experiments were performed with different drying times to investigate the effective of drying time on film thickness and consequential impact on the resulting IR spectral signatures obtained (results discussed in more detail below).

ATR-FTIR Spectroscopy Upon the Prepared Serum Samples

The sample-loaded ATR crystals were then analysed with a JASCO FTIR-410—Specac Golden Gate™ spectrometer to provide a series of spectroscopic signatures between 400-4000 $cm^{-1}$ at at resolution of 4 $cm^{-1}$ using 32 co-added scans for each subjects blood serum samples. IR spectral runs were repeated three times to yield a total of 222 signatures, 3 per subject.

The spectral signatures were then cropped to the fingerprint region between 1800 and 900 wavenumbers ($cm^{-1}$) and vector normalised.

Figure 11:
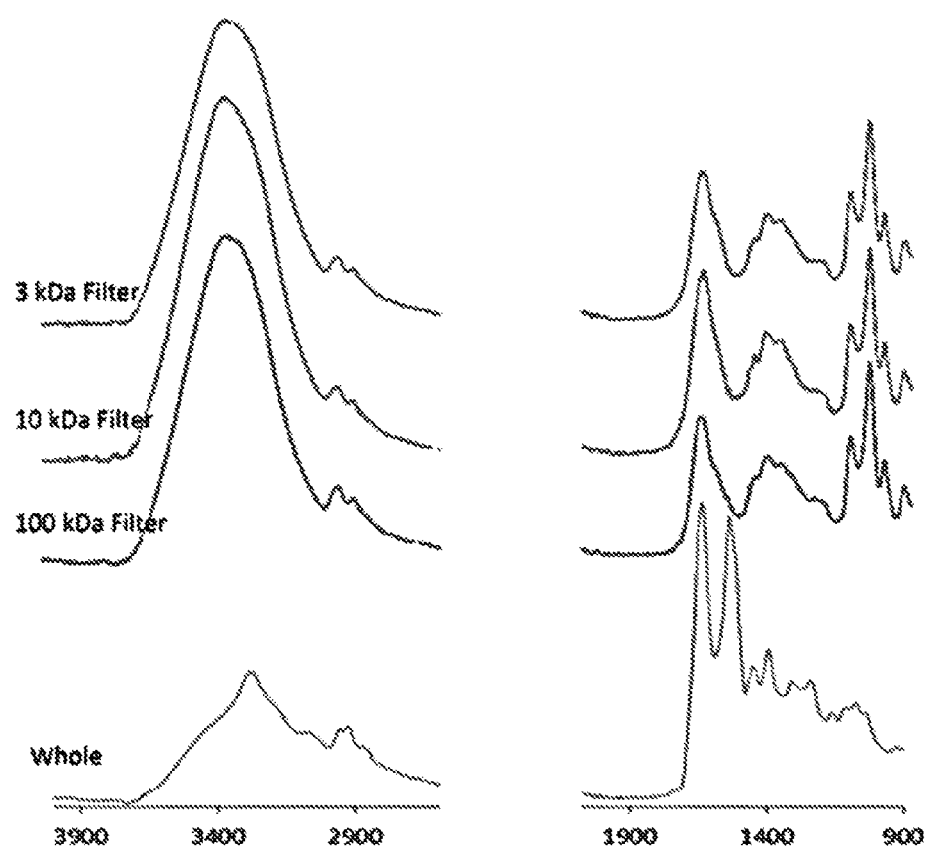
FIG. 11 shows a representative sample of FTIR spectral signatures of each of serum sample types 1-4.

FIG. 11 shows a representative sample of overlayed FTIR spectral signatures of each of serum sample types 1-4. Variance in the fingerprint region (between 900 and 1800 $cm^{-1}$) of the signatures appeared to be the most marked, suggesting a highly relevant information content within this particular region.

Various additional side experiments were performed, running ATR-FTIR spectra of various samples to demonstrate both the viability of ATR-FTIR and the effect of various parameters on the resulting spectral signatures.

ATR-FTIR Side-Experiments to Show Affect of Film Thickness on Certain IR Peaks

ATR-FTIR spectroscopic analysis performed up Bovine Serum Albumin (BSA) has been reported in the literature. Since BSA contains some key components also contained in blood serum, literature IR signatures were considered and compared. Moreover, the literature signatures were considered in the light of BSA and blood serum experiments performed by the inventors.

Figure 12:
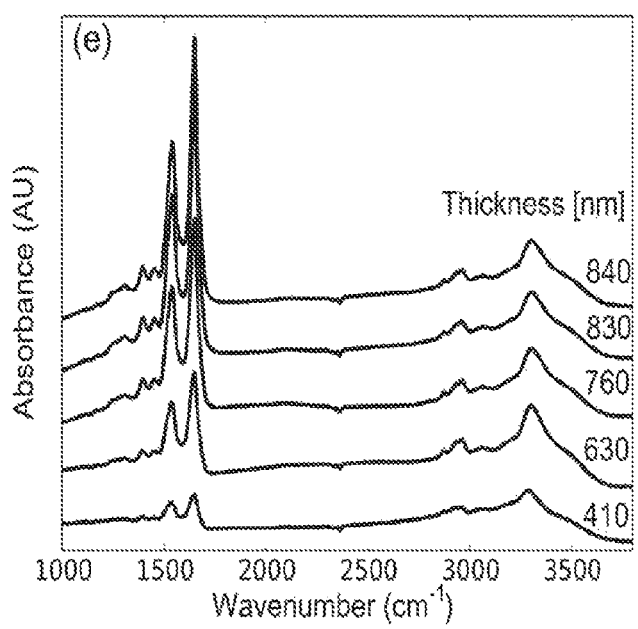
FIG. 12 (taken from Filik J, Frogley M D, et al. *Analyst*, 2012, 137, 853) shows overlayed FTIR spectral signatures of samples of Bovine Serum Albumin (BSA) at different mean film thicknesses on the ATR crystal.

FIG. 12 (taken from Filik J, Frogley M D, et al. *Analyst*, 2012, 137, 853) shows overlayed FTIR spectral signatures of samples of Bovine Serum Albumin (BSA) at different mean film thicknesses on the ATR crystal. There is clear variation with film thickness in the spectral signature in the 900-1800 $cm^{-1}$ fingerprint region.

Figure 13:
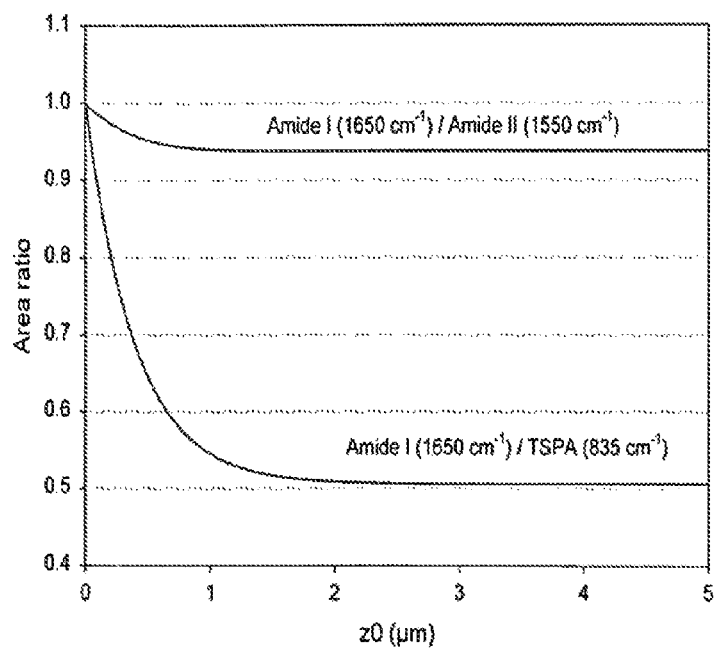
FIG. 13 (taken from Goormaghtigh E, et al. *Biochimica et Biophysica Acta*, 1999, 1422, 105) is a graphical representation showing how area ratios of a) two characteristic amides present in serum samples, Amide I (1650 cm$^{-1}$) and Amide II (1550 cm$^{-1}$) vary with BSA film thickness, and b) Amide I (1650 cm$^{-1}$) and TSPA internal standard (835 cm$^{-1}$) vary with BSA film thickness.

FIG. 13 (taken from Goormaghtigh E, et al. *Biochimica et Biophysica Acta*, 1999, 1422, 105) is a graphical representation showing how area ratios of a) two characteristic amides present in serum samples, Amide I (1650 $cm^{-1}$) and Amide II (1550 $cm^{-1}$) vary with BSA film thickness, and b) Amide I (1650 $cm^{-1}$) and TSPA internal standard (835 $cm^{-1}$) vary with BSA film thickness. These amides are believed to be important in the diagnosis of gliomas from blood serum, since changes in these peaks appears to be indicative of a protein structure change related to the presence or otherwise of glioma in a subject. However, FIG. 13 demonstrates that sample thickness can also affect such peaks. It was therefore seen by the inventors as desirable to eliminate or account for the effect of sample thickness variation to improve the utility of spectroscopy in the diagnosis of proliferative disorders such as gliomia.

The inventors discovered that the Amide I and II ratios remained substantially constant between BSA samples when samples were prepared upon the ATR plate at a thickness of 0.8 microns. The inventors have furthermore shown that Amide I and II ratios remained substantially constant between whole blood serum samples taken from subjects in the same category (i.e. whether both healthy or both having glioma) when samples were prepared upon the ATR plate at a thickness of 0-40 microns (as described above). Moreover, the inventors have shown that Amide I and II ratios remained substantially constant between blood serum samples type 3 (i.e. with components over 10 kDa removed) taken from subjects in the same category (i.e. whether both healthy or both having glioma) when samples were prepared upon the ATR plate at a thickness of 2-8 microns (as described above).

Therefore, these results show that ATR-FTIR spectroscopy upon blood serum samples is a viable method of discerning glioma patients from healthy patients, though optimising sample preparation is crucial to optimise results. Sample thickness upon the ATR plate appears to be of particular relevance to the diagnostic quality of the signatures.

ATR-FTIR Side-Experiments Demonstrating Effect of Sample Drying Time on IR Signatures Several ATR-FTIR spectroscopic analyses were performed upon the same whole human serum but with different levels of drying upon the ATR crystal prior to analysis. After application to the ATR crystal, as described above, serum samples were dried for 0, 2, 4, 6, 8, 16, and 32 minutes at room temperature (25° C.) upon the surface of the ATR crystal before spectroscopical analysis was performed.

Figure 14:
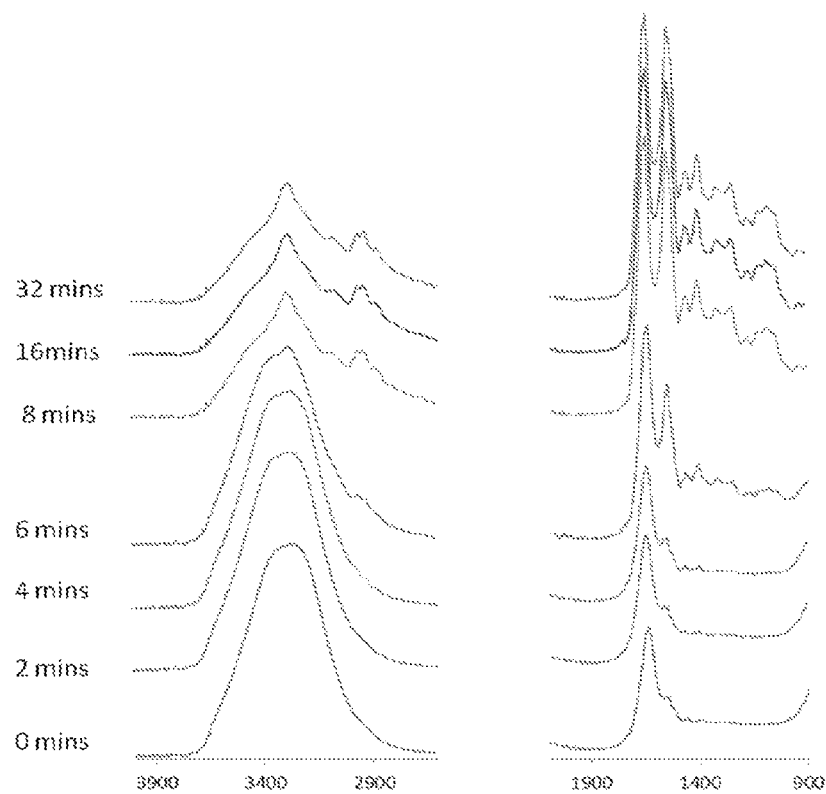
FIG. 14 shows various overlayed spectroscopic signatures of whole human serum dried at room temperature for 0, 2, 4, 6, 8, 16, and 32 minutes.

FIG. 14 shows various overlayed spectroscopic signatures of whole human serum dried at room temperature for 0, 2, 4, 6, 8, 16, and 32 minutes. The drier the film the more information appears to be present in the finger print region between 900-1800 $cm^{-1}$, and thus the more suitable said signatures are for diagnostic analysis in relation to gliomas. However, there is a trade off for long drying times, since the inventors seek to provide a diagnostic tool which rapidly diagnoses proliferative disorders via spectroscopy. As such, drying times between 6 and 12 minutes, preferably around 8 minutes would appear to be optimal, since little extra information is gained in the fingerprint region above 8 minutes of drying time.

Post-Processing of Spectral Signatures of Serum Samples

All of the spectral signatures and corresponding factual information (e.g. medical condition, sex, age, etc.) associated with both the glioma patients and healthy subjects are uploaded to a database, such as MATLAB™ in order that they can be recalled, tested, statistically analysed, or even used as a comparative data set for testing as yet uncorrelated signatures.

The 74 spectral signatures (×3) obtained for serum type 1 samples (whole serum samples for the 74 subjects, all dried in accordance with the optimised 8 minute protocol described above) were split into a "training set" (two thirds) and a "blind set" (one third):

33 training, and 16 blind for signatures of whole serum samples taken from the 49 Grade IV gliomblastoma patients; and 17 training, 8 blind for signatures of whole serum samples taken from the 25 healthy subjects.

The training sets were then used to establish a predictive model using two different pattern recognition algorithms:

1) A Support Vector Machine (SVM)—e.g. RBF, see Baker et al. *Analyst* 2010 135(5), Sattlecker et al. *Analyst* 2010 135(5); and
2) Principal Component Discriminant Function Analysis (PC-DFA).

The signatures, once separated into a "training set" of signatures and a "blind set" of signatures can be used to develop a powerful predictive model that can assign a favourable or unfavourable diagnosis to a non-assigned signature. The "training set" is trained using pattern recognition algorithms by performing a grid search to optimise the cost and gamma functions to ensure that it can identify a training set, to thereby produce a viable predictive model. The "blind set" is then offered to the model, which is then asked to predict whether the individual signatures in the blind set should correlate to a favourable or unfavourable diagnosis and/or prognosis. The predictions can then be translated into a "confusion matrix" illustrating which predictions were made. These predictions can then be validated (e.g. by verifying the actual result, e.g. from a biopsy) to calculate the sensitivity and specificity of the model.

Figure 15:
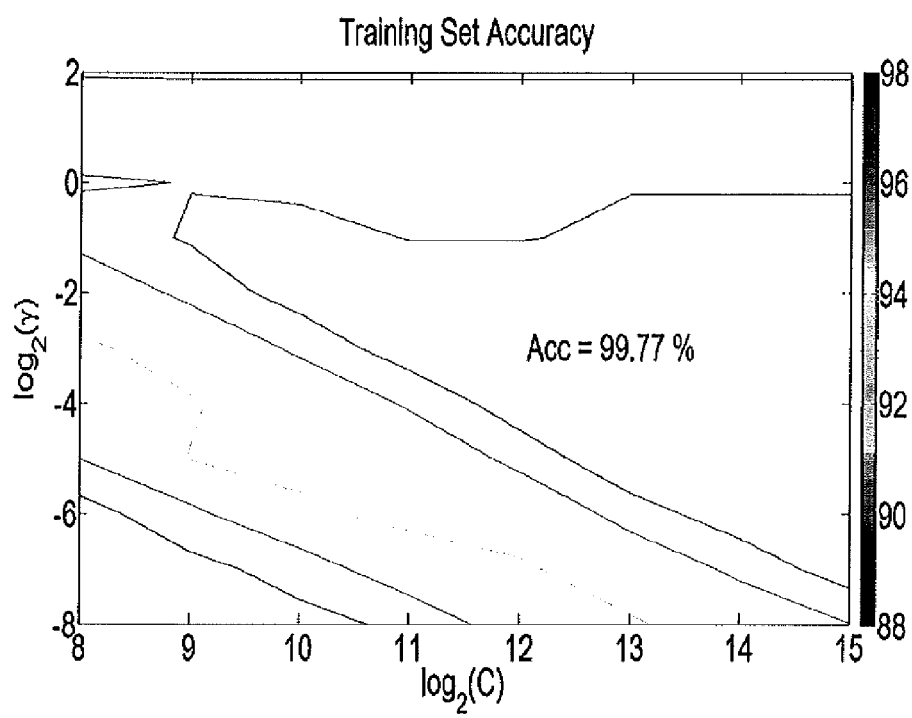
FIG. 15 is a graphical chart illustrating the training set accuracy of the whole serum predictive model when the "blind set" is assessed using the predictive model.

FIG. 15 is a graphical chart illustrating the training set accuracy of the whole serum predictive model when the "blind set" is assessed using the predictive model. When using the predictive model, generated by the training set, to assign a diagnosis to the "blind set" signatures, 21 out of 216 spectra (i.e. where the 3 repeat spectras were all used) were misclassified, giving rise to a sensitivity of 88.19% and a specificity of 94.44%.

The same training was performed on 74 spectral signatures (×3) obtained for serum type 3 samples (with components of a molecular weight above 10 kDa removed), which were again all dried in accordance with the optimised 8 minute protocol described above. These were again split into a "training set" (two thirds) and a "blind set" (one third) exactly as described above in relation to serum type 1 samples.

Figure 16:
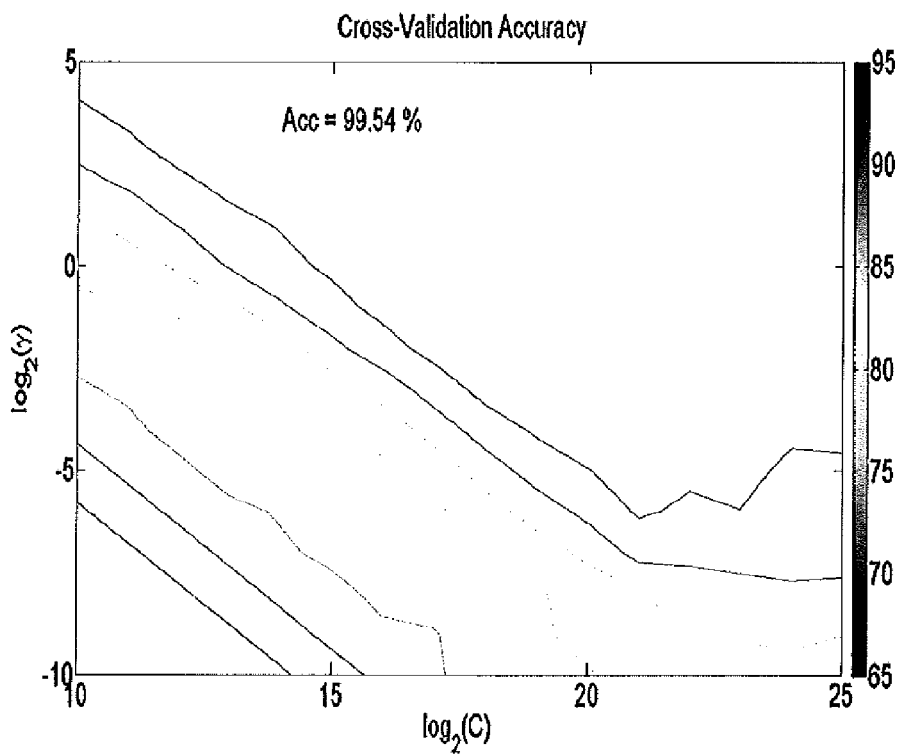
FIG. 16 is a graphical chart illustrating the training set accuracy of the serum type 3 predictive model when the relevant "blind set" was assessed against the predictive model.

FIG. 16 is a graphical chart illustrating the training set accuracy of the serum type 3 predictive model when the relevant "blind set" was assessed against the predictive model. When using the predictive model, generated by the training set, to assign a diagnosis to the "blind set" signatures, 38 out of 216 spectra (i.e. where the 3 repeat spectras were all used) were misclassified, giving rise to a sensitivity of 78.9% and a specificity of 88.9%.

As such, it appears serum type 1 (whole serum) yields a better predictive model than serum type 3 in terms of overall sensitivity and specificity. This simplifies the diagnostic methods of the invention even further, since there would be no need to further process the whole serum in order to obtain reliable diagnostic results.

These results demonstrate the excellent diagnostic potential of spectroscopic signatures in relation to proliferative disorders such as glioma. Clearly the predictive models described could be further refined by training larger database sets of signatures. More refined databases may additionally contain further factual information regarding the subjects in question, which could enable more patient-specific predictions. Signature databases could easily be used alone or in conjunction with a predictive model to correlate non-assigned signatures with a favourable or unfavourable diagnosis, for instance by "best fit" comparisons.

Predictive models such as those described herein can be readily incorporated into computer software installed upon an on-board computer of a diagnostic kit so as to provide a simple diagnostic kit capable of performing a rapid diagnosis. Such a diagnostic kit may incorporate a spectroscopic device or be otherwise capable of communicating with a spectroscopic device (or its associated signature storage unit) in order that predictive algorithms can be run on acquired blood serum signatures. Due to the contribution made to the art by the present invention, it is now easy to envisage how a simple, cost-effective diagnostic kit can be produced which allows rapid diagnosis of proliferative disorders from a mere blood sample. The diagnostic kit may be readily adapted, using techniques known in the art, to include a range of functionality to automate any or all of the method steps described herein.

It is also easy to envisage how the spectroscopic diagnostic kits described herein could be used in conjunction with the assay kits to provide highly accurate, reliable, and well validated diagnoses without the need for invasive biopsies or costly imaging. Alternatively, the diagnostic methods and kits described herein could be used for pre-screening before expensive and/or invasive diagnostic methods are employed.

Example 2A

Spectroscopic Analysis of a Blood Sample

Methods and Materials
Serum Samples

Blood samples were collected from 49 patients diagnosed with a Glioblastoma Multiforme (GBM) brain tumour (i.e. high-grade), 23 patients with a diagnosed low-grade glioma (astrocytoma, oligoastrocytoma, oligodendroglioma) and 25 normal (non-cancer) patients. Samples were obtained from the Walton Research Tissue Bank and Brain Tumour North West (BTNW) Tissue Bank where all patients had given research consent. Blood sample details are outlined in Table 16 below.

All blood samples were taken pre-operatively. The serum tubes were left to clot at room temperature for a minimum of 30 minutes and a maximum of 2 hours from blood draw to centrifugation. Separation of the clot was accomplished by centrifugation at 1,200 g for 10 minutes and 500 µl aliquots of serum dispensed into prelabelled cryovials. Serum samples were snap frozen using liquid nitrogen and stored at −80° C.

The average age of the entire sample set is 54.62 years. Where possible, age and sex of the GBM and control serum samples were matched.

TABLE 16

Blood Sample Details

| Tumour Grade | Number of Subjects | Age range/mean age | Gender |
|---|---|---|---|
| Normal (Non-cancer) | 25 | 26-87/59.1 years | 29 male, 20 female |
| Low-Grade | 23 | 19-60.3/36.9 years | 11 male, 12 female |
| High-Grade | 49 | 24.7-78.8/60.1 years | 15 male, 10 female |

Drying Study

Normal human mixed pooled serum (0.2 µL sterile filtered, CS100-100, purchased from TCSBiosciences, UK) was used in a volumes of 1 µL to determine the optimal drying time necessary for quality spectral collection.

Spectra were collected using a JASCO FTIR-410 spectrometer equipped with a Specac ATR single reflection diamond Golden Gate™ at the University of Central Lancashire, in the range of 4000-400 $cm^{-1}$, at a resolution of 4 $cm^{-1}$ and over 32 co-added scans. Prior to each spectral collection, a background absorption spectrum was collected for atmospheric correction.

1 µL of serum was pipetted onto the ATR-FTIR crystal and a spectrum was collected at 0, 2, 4, 8, 16 and 32 minute intervals to observe spectral changes during the drying process. The dried intimate serum film was wiped off the crystal using absolute ethanol (purchased from Fisher Scientific, Loughborough, UK). One biological repeat and two technical repeats were collected per 1 µL of dried serum. The drying experiment was repeated multiple times to gain spectra representative at specific times during drying.

Variance Study

Normal human mixed pooled serum (0.2 µL sterile filtered, CS100-100, purchased from TCSBiosciences, UK) was used in the variance study where 1 µL was pipetted on to the ATR-FTIR single reflection diamond crystal and dried for 8 minutes, at which time 3 spectra were collected. Three spectra were collected per 1 µL and repeated 50 times. The dried serum spot was wiped off the crystal between each variance repeat with absolute ethanol (purchased from Fisher Scientific, Loughborough, UK). In total, 150 ATR-FTIR spectra were collected from the variance study.

ATR-FTIR Spectral Diagnostic Model

All whole serum samples were thawed prior to spectral collection and 100 kDa, 10 kDa and 3 kDa filtration aliquots were prepared using Amicon Ultra-0.5 mL centrifugal filters (purchased from Millipore Limited, UK) [FIG. 1]. Centrifugal filters filter out components of the serum above the cut-off point of the filters membrane (i.e. 100 kDa), allowing components below the filter membrane cut-off point to pass through.

Figure 17:
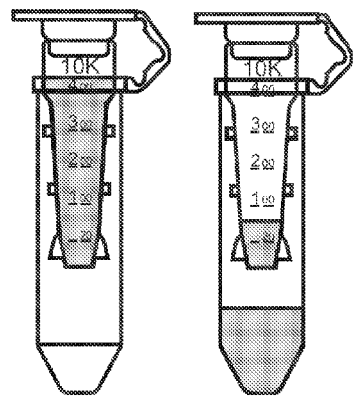
FIG. 17 shows 0.5 ml of serum in a centrifugal filter (left) and centrifuged so that the filter retains all serum constituents greater than the kilodalton range (100, 10 or 3 kDa), only allowing through the serum filtrate which contains constituents below the maximum range.

FIG. 17 shows 0.5 ml of serum being pipetted into a centrifugal filter (left) and centrifuged so that the filter retains all serum constituents greater than the kilodalton range (100, 10 or 3 kDa), only allowing through the serum filtrate which contains constituents below the maximum range.

Each whole serum sample (high-grade, low-grade and control) had a filtration aliquot prepared by pipetting 0.5 mL of the whole serum in to the filtration device and centrifuging at 14,000 rpm for; 10 minutes, 15 minutes, and 30 minutes for 100 kDa, 10 kDa and 3 kDa filter devices, respectively.

Spectra were collected in a random order within the serum sample sets. For each sample, a 1 µL serum spot was dried for 8 minutes on the ATR-FTIR crystal, at which time 3 spectra were collected. This procedure was repeated three times per sample. As a result, for each sample 9 spectra were collected. Prior to spectral collection, a background absorption spectrum was collected (for atmospheric correction) before the 1 µL was pipetted onto the ATR-FTIR crystal, thus a background was collected per serum replicate. The dried serum film was washed off the crystal in between each procedure using Virkon® disinfectant (purchased from Antec Int., Suffolk, UK) and absolute ethanol (purchased from Fisher Scientific, Loughborough, UK)

Spectra were acquired in the range of 4000-400 $cm^{-1}$, at a resolution of 4 $cm^{-1}$ and averaged over 32 co-added scans. In total, 3375 ATR-FTIR spectra were collected from all whole and filtration serum samples. Table 2 shows the total number of spectra and patients in each serum grade and filtration category.

TABLE 17

The number of spectra collected and number of patients (in brackets) for each filtrate composition for the range of cancer serum severities being analysed.

| | Whole Serum | 100 kDa Serum | 10 kDa Serum | 3 kDa Serum |
|---|---|---|---|---|
| High-Grade Serum | 441 (49) | 423 (47) | 423 (47) | 405 (45) |
| Low-Grade Serum | 207 (23) | 207 (23) | 198 (22) | 198 (22) |
| Normal (Non-cancer) Serum | 225 (25) | 225 (25) | 225 (25) | 198 (22) |

Data Analysis

Pre-processing and multivariance (MVA) analysis was carried out on the raw spectral data in Matlab™ (7.11.0 (R2010b) (The MathWorks, Inc. USA) using in-house written software.

Results

Drying Study

Figure 18:
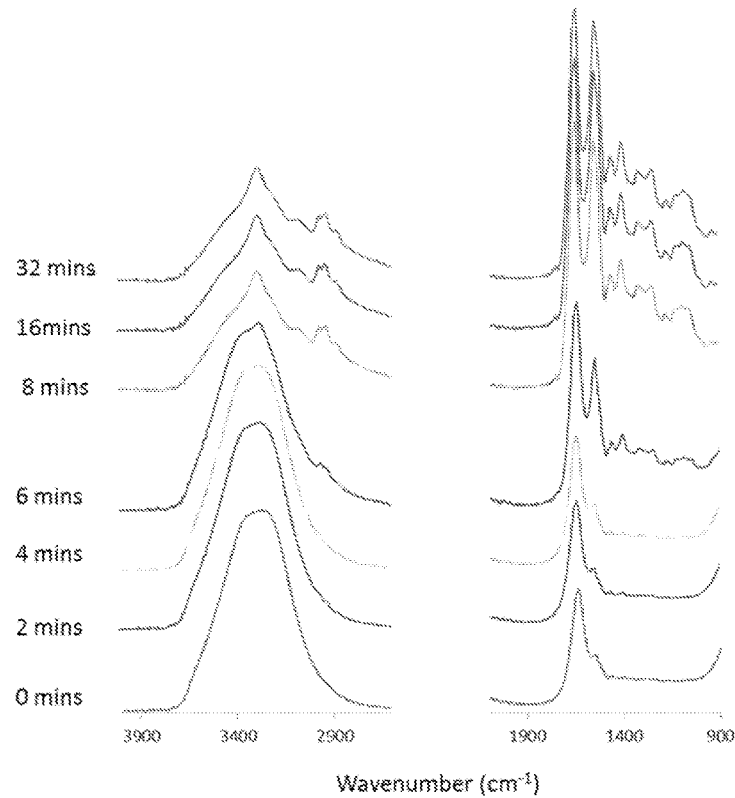
FIG. 18 shows various overlayed ATR-FTIR spectroscopic signatures of whole human serum dried at room temperature for 0, 2, 4, 6, 8, 16, and 32 minutes. The spectra have been offset for ease of visualization.
Figure 19A:
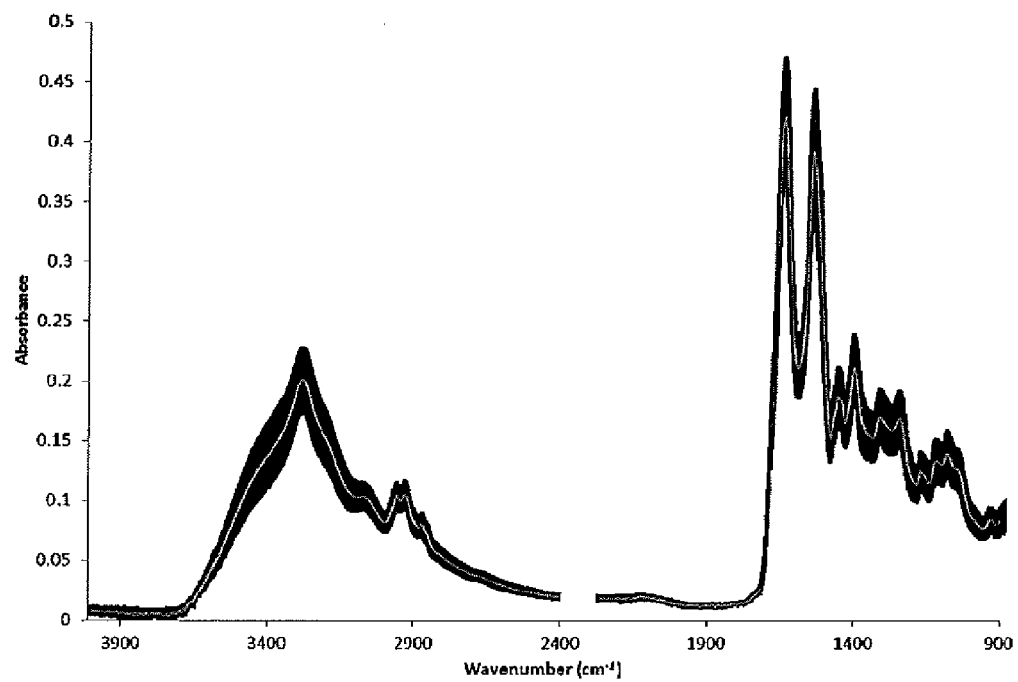
FIGS. 19A-D shows raw and unprocessed spectral data for (A) whole serum spectrum (900-3900 $cm^{-1}$) and the (B) fingerprint region (900-1800 $cm^{-1}$) compared to pre-processed data (noise reduction (30 PCs) and vector normalization) (C) pre-processed whole serum spectrum and (D) pre-processed fingerprint region. The variable $CO_2$ region (2300-2400 $cm^{-1}$) has been removed.
Figure 19B:
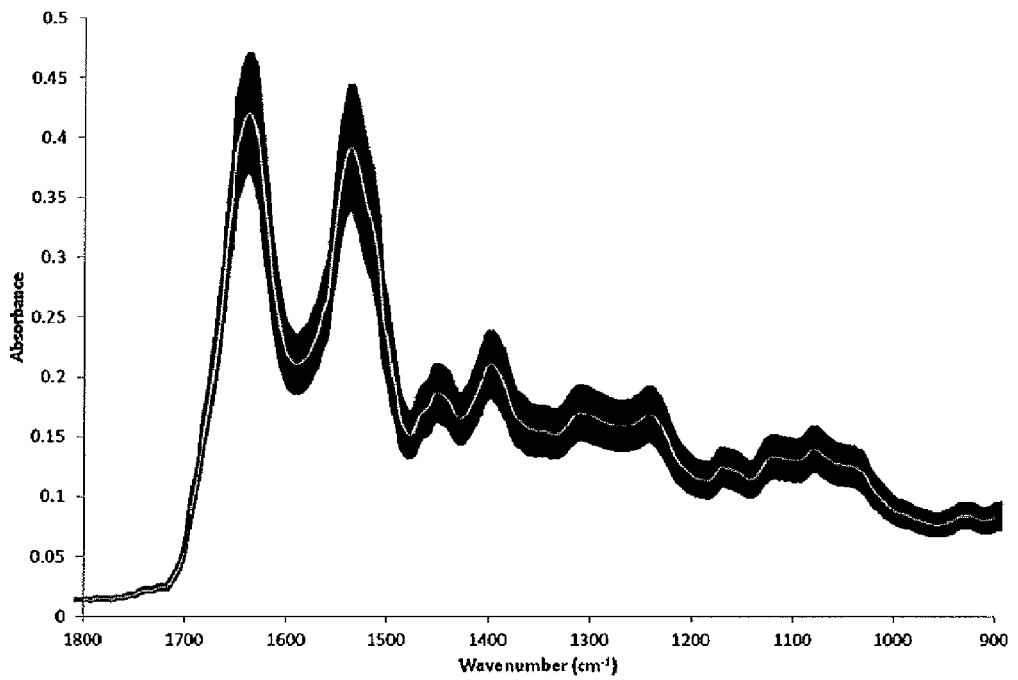
Figure 19C:
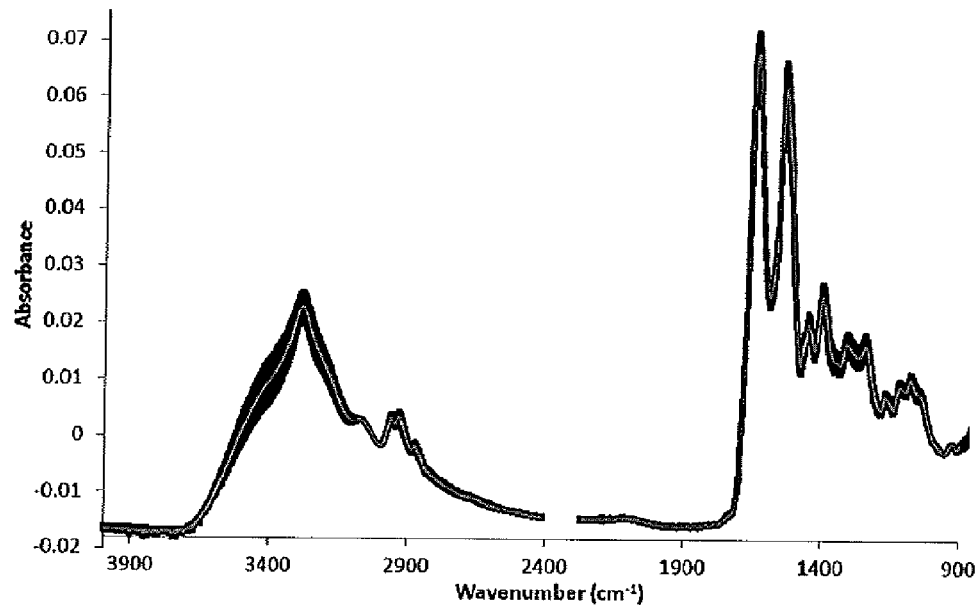
Figure 19D:
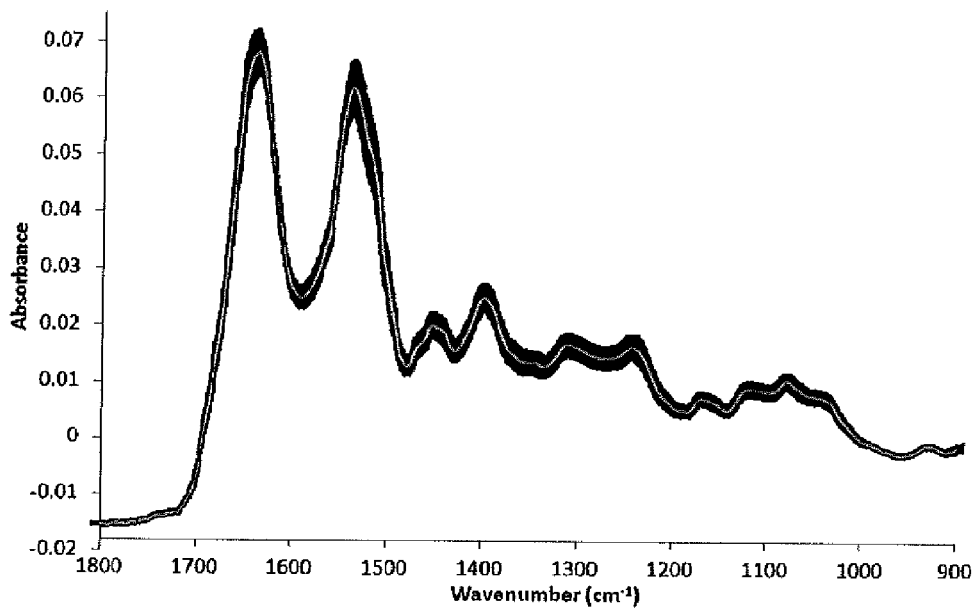

FIG. 18 shows various overlayed ATR-FTIR spectroscopic signatures of whole human serum dried at room temperature for 0, 2, 4, 6, 8, 16, and 32 minutes. The spectra have been offset for ease of visualization FIG. 18 displays the typically observed ATR-FTIR spectral data from 1 µL of whole human serum over a range of 0-32 minutes during drying. The spectra have been offset for ease of visualisation. At room temperature (~18° C.) 1 µL of serum has been found to dry after 8 minutes through repeat drying experiments. Effective spectral collection requires intimate contact between the serum sample and the ATR-FTIR crystal to allow interaction with the evanescent field; this can be achieved by allowing the liquid serum sample to dry. Drying allows the intensity of the bands to increase exponentially as swelling decreases, thus reducing the distance between the reflecting interference (water) and the sample molecules.

Variance Study

FIGS. 19A-D shows raw and unprocessed spectral data for (A) whole serum spectrum (900-3900 $cm^{-1}$) and the (B) fingerprint region (900-1800 $cm^{-1}$) compared to pre-processed data (noise reduction (30 PCs) and vector normalization) (C) pre-processed whole serum spectrum and (D) pre-processed fingerprint region. The variable $CO_2$ region (2300-2400 $cm^{-1}$) has been removed. The four spectra display an average spectrum surrounded by a standard deviation (STD) error margin. The largest variance between the raw (unprocessed) spectral data was at 1637.27 $cm^{-1}$ (STD: 0.4209) in both analysed wavenumber regions. The smallest variance in the raw data was at 3735.44 $cm^{-1}$ (STD: 0.0038) between 3900-900 $cm^{-1}$ and at 1792.51 $cm^{-1}$ (STD: 0.0138) in the fingerprint region. Noise reduction (30 principle components) and vector normalization pre-processing methods were applied to the data to reduce the baseline and to smooth the data. The pre-processing methods significantly reduced the STD and variance of the spectral data. The largest raw data STD at 1637.27 $cm^{-1}$ was reduced from 0.4209 to 0.0043 (pre-processed), a difference of 195.9%. The smallest spectral variance STDs were reduced from 0.0038 to 0.00123 at 3735.44 $cm^{-1}$ and from 0.0138 to 0.0004 at 1792.51 $cm^{-1}$. The average STD across the 3900-900 $cm^{-1}$ raw and pre-processed data was 0.0137 and 0.0015 respectively. The STD values of the raw spectra were low initially but were reduced further by implementing pre-processing methods. The reproducibility of spectral data using ATR-FTIR is high and exhibits minimal variance, especially after pre-processing.

Pre-Processing Selection Data

For each whole and filtration serum sample set, an identical approach was used to pre-process the spectral data, and to analyse using multivariate analysis methods. Firstly, to remove any bias from analysis models, the technical replicates from each sample were averaged so that each serum sample set contained three spectra from each patient; one average spectrum from each patient spot. Outliers were then removed from the spectral sets using a quality test discriminating abnormal spectral data. In this case, quality controlled spectra often corresponded to specific patients.

A principal component based noise reduction, using the first 30 principal components of the data, was performed on the spectra to improve the signal-to-noise ratio. Following this, all spectra were vector normalised and mean centred. The spectral data was also analysed using second derivative spectra of the data, but best overall results for PCA and SVMs were achieved using the noise reduction, vector normalisation and mean centring process.

Principal component analysis (PCA) was performed on the pre-processed spectra, giving an unsupervised classification from which the loadings could be interpreted. Support vector machines (SVM) were also applied to the data sets using a radial based function (RBF) kernel. Using LIBSVM code in MATLAB, (Chih-Chung Chang and Chih-Jen Lin, LIBSVM: a library for support vector machines. ACM Transactions on Intelligent Systems and Technology, 2:27: 1-27:27, 2011. Software available at http://www.csie.nt-u.edu.tw/~cjlin/libsvm) an automatic n-fold cross validation was performed on the data to find the best values for the cost and gamma functions. These values were then used to train the SVM in one-versus-rest mode using a randomly selected training set consisting of two thirds of the patient-associated spectral data. The remainder of the data, making up the blind test set, was then projected into the model, and confusion matrices were calculated giving an overall SVM classification accuracy based on the true and predicted data class labels. Sensitivities and specificities were calculated for each SVM model and for each separate disease group.

The results presented in Tables 18, 19, and 20 below were derived from three different test and blind spectral sets to provide a range of sensitivities and specificities for whole serum.

TABLE 18

Statistical Analysis for Test 1 on Whole Serum

| 1 (Best Serum) | Normal Optimum | Normal Range | Low | Low Range | High | High Range | Overall Average | Overall Range |
|---|---|---|---|---|---|---|---|---|
| Patient sensitivity | 100 | 75.00-100.00 | 87.5 | 87.50-87.50 | 93.75 | 92.86-93.75 | 93.75 | 75.00-100.00 |
| Patient specificity | 95.83 | 95.45-100.00 | 100 | 95.45-100.00 | 93.75 | 87.50-93.75 | 96.53 | 87.50-100.00 |
| Spectra sensitivity | 95.83 | 78.26-95.83 | 86.36 | 85.00-91.67 | 95.65 | 92.86-95.65 | 92.61 | 78.26-95.83 |
| Spectra specificity | 97.06 | 95.45-100.00 | 100 | 95.45-100.00 | 91.30 | 86.36-91.30 | 96.12 | 86.36-100.00 |

BEST SVM:
C = 22.63,
Gamma = 4,
Training accuracy = 85.86%,
SVM total accuracy = 96.875%

TABLE 19

Statistical Analysis for Test 2 on Whole Serum

| 2 | Normal | Low | High | Overall Average |
|---|---|---|---|---|
| Patient sensitivity | 75 | 87.50 | 92.86 | 85.12 |
| Patient specificity | 95.45 | 95.45 | 87.5 | 92.80 |
| Spectra sensitivity | 78.26 | 91.67 | 92.86 | 87.60 |
| Spectra specificity | 95.45 | 96.88 | 89.13 | 93.82 |

TABLE 20

Statistical Analysis for Test 3 on Whole Serum

| 3 | Normal | Low | High | Overall Average |
|---|---|---|---|---|
| Patient sensitivity | 87.5 | 87.5 | 93.33 | 89.44 |
| Patient specificity | 100 | 95.65 | 87.5 | 94.38 |

TABLE 20-continued

Statistical Analysis for Test 3 on Whole Serum

| 3 | Normal | Low | High | Overall Average |
|---|---|---|---|---|
| Spectra sensitivity | 87.5 | 85 | 93.18 | 88.56 |
| Spectra specificity | 100 | 95.45 | 86.36 | 93.94 |

The results presented in Table 21 below were derived from a corresponding test on 100 kDa filtered serum.

TABLE 21

Statistical Analysis for Test on 100 kDa filtered serum

| | Normal | Low | High | Overall Average |
|---|---|---|---|---|
| Patient sensitivity | 50 | 57.14 | 100 | 69.05 |
| Patient specificity | 95.45 | 95.45 | 66.7 | 85.87 |
| Spectra sensitivity | 54.17 | 61.90 | 93.75 | 69.94 |
| Spectra specificity | 94.12 | 94.12 | 67.44 | 85.39 |

BEST SVM: C = 2048,
Gamma = 0.85,
Training accuracy = 72.58%,
SVM total accuracy = 79.57%

ABBREVIATIONS

ATR—Attenuated Total Reflection
Basic FGF—Basic fibroblast growth factor
β-NGF—Nerve growth factor-beta
CTACK—Cuteaneous T-Cell attracting chemokine;
FTIR—Fourier Transfer Infra-red
G-CSF—Granulocyte-colony stimul.factor
GM-CSF—Granulocyte-macrophage colony stimulating factor
GRO—Growth related oncogene
GRO-α—Growth related oncogene-α
HGF—Hematopoietic growth factors,
ICAM-1—Intercellular adhesion molec. 1
IFN-gamma—Interferon gamma
IGFBP-1—Insulin-like growth factor-binding protein 1
IL-1α—Interleukin 1 alpha
IL-1β—Interleukin 1 beta
IL-1rα—Interleukin 1 receptor antagon.
IL-1 R1—Interleukin 1 receptor-rel.prot 1
IL-1 R4/ST2—Interleukin 1 receptor 4, ST2
IL-2—Interleukin 2
sIL-2 Rα—Interleukin 2 soluble receptor α
IL-3—Interleukin 3
IL-4—Interleukin 4
IL-5—Interleukin 5
IL-6—Interleukin 6
IL-6 R—Interleukin 6 receptor
IL-7—Interleukin 7
IL-8—Interleukin 8
IL-10—Interleukin 10
IL-11—Interleukin 11
IL-12p40—Interleukin 12p40
IL-12p70—Interleukin 12p70
IL-13—Interleukin 13
IL-15—Interleukin 15
IL-16—Interleukin 16
IL-17—Interleukin 17
IL-18—Interleukin 18
IR—Infra-red
MCP-1—Monocyte chemoattractant protein 1
MCP-3—Monocyte chemoattractant p.3
M-CSF—Macrophage-colony stimulating factor
MIF—Macrophage migration inhibitory factor
MIG—Monokine induced by gamma interferon
MIP-1α—Macrophage inflammatory p-1α
MIP-1β—Macrophage inflammatory p-1β
MIP-1δ—Macrophage inflammatory p-1δ
MIP-3α—Macrophage inflammatory p-3α
MIP-3β—Macrophage inflammatory p-3β
MSP-α—Macrophage stimulating protein a-chain
PAI-1—Plasminogen activator inhibitor 1
PDGF AA—Platelet-derived growth factor
PDGF-BB—Platelet-derived growth factor
PIGF—Placenta growth factor
RANTES—Regulated upon activation, normal T-cell expressed
SCF—Stem cell factor
SDF-1—Stromal cell-derived factor
sgp130—Soluble glycoprotein 130
sHER2 neu—Human Epidermal Growth Factor Receptor 2
sIL-6R alpha—soluble Interleukin-6 receptor alpha
sTNF RI—Soluble TNF receptor I
sTNF RII—Soluble TNF receptor II
sVEGFR1—soluble vascular endothelial growth factor receptor 1
TARC—Thymus and activation regulated chemokine
TECK—Thymus-expressed chemokine
TGF-beta 1—Tumor necrosis factor beta 1
TGF-beta 3—Tumor necrosis factor beta 3
TIMP-1—Tissue inhibitor of metalloprot 1
TIMP-2—Tissue inhibitor of metalloprot 2
TNF-α—Tumor necrosis factor-alpha
TNF-β—Tumor necrosis factor-beta
TPO—Thrombopoietin
TRAIL R3—TNF-related apoptosis inducing ligand receptor 3
TRAIL R4—TNF-related apoptosis inducing ligand receptor 4
VEGF—Vascular endothelial growth f.
VEGF C—vascular endothelial growth factor C
VEGF-D—Vascular endothelial growth f-D.

What is claimed is:

1. A method of treating a glioma in a subject, the method comprising assaying a blood sample or a component thereof of the subject in respect of two or more predesignated cytokines and/or angiogenesis factors selected from the group consisting of prolactin, follistatin, PDGF-BB, PECAM-1, IL-8, IL-10, HGF, angiopoietin, leptin, PDGF-AA, sHER2 neu, sIL-6R alpha, sVEGFR1, G-CSF, and FGF, wherein at least one of the predesignated cytokines is selected from the group consisting of prolactin, follistatin, G-CSF, PDGF-BB, and PECAM-1;
   correlating elevated or reduced levels of each of the two or more cytokines
   and/or angiogenesis factors, whether relative to a predetermined threshold or relative to each other, with a favourable or unfavourable diagnosis and/or prognosis of glioma: and
   administering a surgical or therapeutic treatment of glioma to the subject, wherein the subject with an unfavourable diagnosis and/or prognosis of glioma,
   wherein correlating elevated or reduced levels of each of the two or more cytokines and/or angiogenesis factors with a favorable or unfavorable diagnosis and/or prognosis of glioma comprises correlating elevated levels of one of more cytokines and/or angiogenesis factors selected from the group consisting of prolactin, follistatin, G-CSF, PDGF-BB, and PECAM-1, with an unfavorable diagnosis and/or prognosis of glioma; and correlating elevated levels of sIL-6R alpha with an unfavorable diagnosis and/or prognosis of high grade glioma and non-elevated levels of sIL-6R alpha with an unfavorable diagnosis and/or prognosis of low grade glioma.

2. The method of claim 1, wherein the cytokine and/or angeiogenesis factor analytes are selected from the group consisting of PDGF-BB, follistatin, PECAM-1, sHER2 neu, sIL-6R alpha, prolactin, sVEGFR1, and G-CSF.

3. The method of claim 1, wherein the two or more predesignated cytokines and/or angiogenesis factors are selected from the group consisting of prolactin, follistatin, PDGF-BB, PECAM-1 and G-CSF.

4. The method of claim 1, wherein assaying the blood sample or the component thereof of the subject is performed in respect of three or more predesignated cytokines and/or angiogenesis factors selected from the group consisting of prolactin, follistatin, PDGF-BB, PECAM-1, IL-8, IL-10, HGF, angiopoietin, leptin, PDGF-AA, sHER2 neu, sIL-6R alpha, sVEGFR1, G-CSF, and FGF, wherein at least two of the pre-designated cytokines are selected from prolactin, follistatin, G-CSF, PDGF-BB, and PECAM-1.

5. The method of claim 1, wherein correlating the analytical results with a favourable or unfavourable diagnosis and/or prognosis involves an initial comparison of the analytical results with a reference standard or with previous analytic results that have been pre-correlated with a favourable or unfavourable diagnosis and/or prognosis.

6. The method of claim 1, wherein the blood sample is assayed with an immunoassay.

7. The method of claim 1, wherein the blood sample is assayed using a magnetic bead-based multiplex assay designed to measure multiple cytokines and/or angiogenesis factors.

8. The method of claim 7, wherein the assay suitably employs a plurality of fluorescently dyed beads to simultaneously detect multiple cytokines and/or angiogenesis factors in a single assay.

9. The method of claim 1, wherein the method further comprises the step of performing spectroscopic analysis upon a blood sample or a component thereof of the subject to produce a spectroscopic signature characteristic of the blood sample or the component thereof; wherein the spectroscopic analysis is Attenuated Total Reflection FTIR (ATR-FTIR), and wherein ATR crystals support the blood sample during IR analysis;
wherein the spectroscopically obtained signature is optionally further correlated with a favourable or unfavourable diagnosis and/or prognosis based on a predictive model developed by "training" a database of pre-correlated analyses.

10. The method of claim 1, wherein the glioma is low grade glioma.

11. The method of claim 1, wherein the glioma is high grade glioma.

12. The method of claim 1, further comprising the step of diagnosing whether a tumour is malignant or benign.

13. A diagnostic kit for diagnosing and/or prognosing a glioma in a subject, comprising a device configured to receive a blood sample or a component thereof from the subject and to assay the blood sample (or a component thereof) in respect of one or more pre-designated cytokines and/or angiogenesis factors selected from the group consisting of prolactin, follistatin, PDGF-BB, PECAM-1, IL-8, IL-10, HGF, angiopoietin, leptin, PDGF-AA, sHER2 neu, sIL-6R alpha, sVEGFR1, G-CSF, and FGF, wherein at least one of the predesignated cytokines is selected from the group consisting of prolactin, follistatin, G-CSF, PDGF-BB, and PECAM-1; and a device to correlate or facilitate correlation of the amounts of the one or more cytokines and/or angiogenesis factors within the blood sample or the component thereof with a favourable or unfavourable diagnosis and/or prognosis of glioma: wherein the device for correlating or facilitating correlation comprises or is in communication with a computer programmed with diagnostic computer software executable upon the computer, wherein said computer is further programmed to correlate said amounts with a favourable or un-favourable diagnosis and/or prognosis by:
collecting data from the assay of the blood sample:
validating the data as definitive and without artifacts that can arise through variation in sample preparation:
exposing the data to a predictive model, based on pre-correlated assays, and
identifying elevated or reduced levels of each of the one or more cytokines and/or angiogenesis factors relative to a predetermined threshold or relative to each other: and
correlating the identified elevated or reduced levels with a favourable or unfavourable diagnosis and/or prognosis.

14. The diagnostic kit of claim 13, wherein the diagnostic kit further comprises a device configured to perform spectroscopic analysis upon the blood sample or a component thereof of the subject to produce a spectroscopic signature characteristic of the blood sample or the component thereof; and a device to correlate or facilitate correlation of the spectroscopic signature of the blood sample or the component thereof with a favourable or unfavourable diagnosis and/or prognosis; wherein the spectroscopic analysis is Attenuated Total Reflection FTIR (ATR-FTIR), and wherein ATR crystals support the blood sample during IR analysis.

15. The diagnostic kit of claim 13, wherein the device for assaying or analyzing the blood sample is the same as the device for correlating or facilitating correlation of the results.

16. The method of claim 1, wherein the two or more predesignated cytokines and/or angiogenesis factors from the group consisting of prolactin, follistatin, G-CSF, sHER2 neu, sIL-6R alpha, sVEGFR1, and FGF, wherein at least one of the predesignated cytokines is selected from the group consisting of prolactin, follistatin, and G-CSF.

17. The method of claim 1, wherein assaying the blood sample or the component thereof of the subject is performed in respect of three or more predesignated cytokines and/or angiogenesis factors selected from the group consisting of prolactin, follistatin, G-CSF, sHER2 neu, sIL-6R alpha, sVEGFR1, and FGF, wherein at least two of the predesignated cytokines are selected from the group consisting of prolactin, follistatin, G-CSF, and sIL-6R alpha.

18. The method of claim 1, wherein one of the predesignated cytokines is follistatin.

19. The method of claim 1, wherein correlating elevated or reduced levels of each of the two or more cytokines and/or angiogenesis factors with a favorable or unfavorable diagnosis and/or prognosis of glioma comprises correlating elevated levels of follistatin with an unfavorable diagnosis and/or prognosis.

20. The method of claim 1, wherein the two or more cytokines and/or angiogenesis factors comprise at most three cytokines and/or angiogenesis factors.

* * * * *

UNITED STATES PATENT AND TRADEMARK OFFICE
CERTIFICATE OF CORRECTION

PATENT NO.        : 9,664,680 B2
APPLICATION NO.   : 15/059797
DATED             : May 30, 2017
INVENTOR(S)       : Baker et al.

It is certified that error appears in the above-identified patent and that said Letters Patent is hereby corrected as shown below:

In the Claims

In Claim 1, Column 44, Line 57, immediately after "glioma" and immediately before "and" please delete ":" and insert -- ; -- therefor.

In Claim 13, Column 46, Lines 22-23, immediately after "each other" and immediately before "and" please delete ":" and insert -- ; -- therefor.

In Claim 16, Column 46, Line 42, immediately after "angiogenesis factors" and immediately before "from" please insert -- are selected -- therefor.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*